(12) United States Patent
Adams et al.

(10) Patent No.: US 6,258,113 B1
(45) Date of Patent: Jul. 10, 2001

(54) NEEDLE HERNIORRHAPHY DEVICES

(75) Inventors: Ronald D. Adams, Holliston; William J. Shaw, Cambridge, both of MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

(21) Appl. No.: 09/628,364

(22) Filed: Jul. 28, 2000

Related U.S. Application Data

(62) Division of application No. 09/175,169, filed on Oct. 20, 1998, now Pat. No. 6,099,518.

(51) Int. Cl.[7] ................................................. A61M 25/00
(52) U.S. Cl. ....................... 606/192; 604/96.01; 604/915; 623/11.11
(58) Field of Search ................................. 606/192, 190, 606/191, 523, 536, 915; 604/96.01, 97.01; 623/11.11

(56) References Cited

U.S. PATENT DOCUMENTS

| | | |
|---|---|---|
| 4,798,205 | 1/1989 | Bonomo et al. . |
| 4,800,901 | 1/1989 | Rosenberg . |
| 5,196,024 | 3/1993 | Barath . |
| 5,197,971 | 3/1993 | Bonutti . |
| 5,318,586 | 6/1994 | Ereren . |
| 5,320,634 | 6/1994 | Vigil et al. . |
| 5,361,752 | 11/1994 | Moll et al. . |
| 5,400,733 | 3/1995 | Zhu et al. . |
| 5,402,772 | 4/1995 | Moll et al. . |
| 5,411,475 | 5/1995 | Atala et al. . |
| 5,425,357 | 6/1995 | Moll et al. . |
| 5,439,476 | 8/1995 | Frantzides . |
| 5,450,843 | 9/1995 | Moll et al. . |
| 5,452,732 | 9/1995 | Bircoll . |
| 5,454,367 | 10/1995 | Moll et al. . |
| 5,465,711 | 11/1995 | Moll et al. . |
| 5,466,221 | 11/1995 | Zadini et al. . |
| 5,490,839 | 2/1996 | Wang et al. . |
| 5,496,345 | 3/1996 | Kieturakis et al. . |
| 5,514,075 | 5/1996 | Moll et al. . |
| 5,520,609 | 5/1996 | Moll et al. . |
| 5,527,264 | 6/1996 | Moll et al. . |
| 5,540,711 | 7/1996 | Kieturakis et al. . |
| 5,562,603 | 10/1996 | Moll et al. . |
| 5,575,759 | 11/1996 | Moll et al. . |
| 5,601,590 | 2/1997 | Bonutti et al. . |
| 5,607,443 | 3/1997 | Kieturakis et al. . |
| 5,613,939 | 3/1997 | Failla . |
| 5,616,149 | 4/1997 | Barath . |
| 5,634,883 | 6/1997 | Chin et al. . |
| 5,643,178 | 7/1997 | Moll et al. . |
| 5,716,408 | 2/1998 | Eldridge et al. . |
| 5,716,409 | 2/1998 | Debbas . |
| 5,766,246 | 6/1998 | Mulhauser et al. . |
| 5,769,864 | 6/1998 | Kugel . |

FOREIGN PATENT DOCUMENTS

WO 97/22310   6/1997   (WO) .

*Primary Examiner*—John D. Yasko
(74) *Attorney, Agent, or Firm*—Hoffman & Baron, LLP

(57) ABSTRACT

Guidewire-deliverable devices and methods of using the devices for separating adjacent layers of tissue and for delivering a surgical prosthesis to an operating site. A guidewire-deliverable cannula provides an elongate window for accessing the operating site with a tissue-separating device. The tissue-separating device may include one of several types of an inflatable balloon or a tissue-dissecting member. The tissue-separating balloon may simultaneously deliver the prosthesis during tissue separation and may further be detached to remain with the prosthesis over the operating site. Alternatively, the prosthesis may be separately provided after the adjacent layers of tissue have been separated.

20 Claims, 29 Drawing Sheets

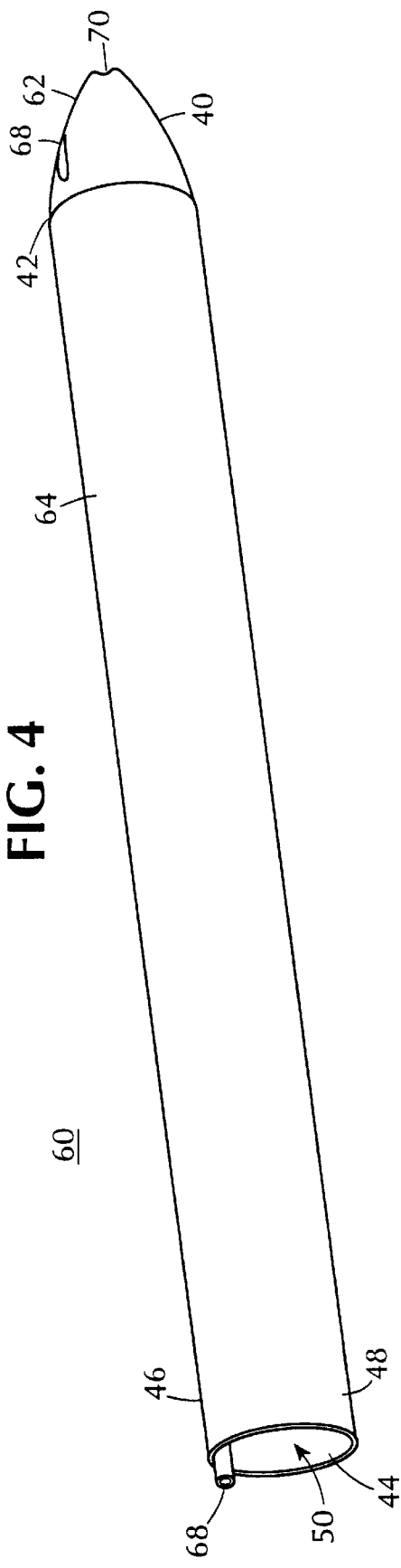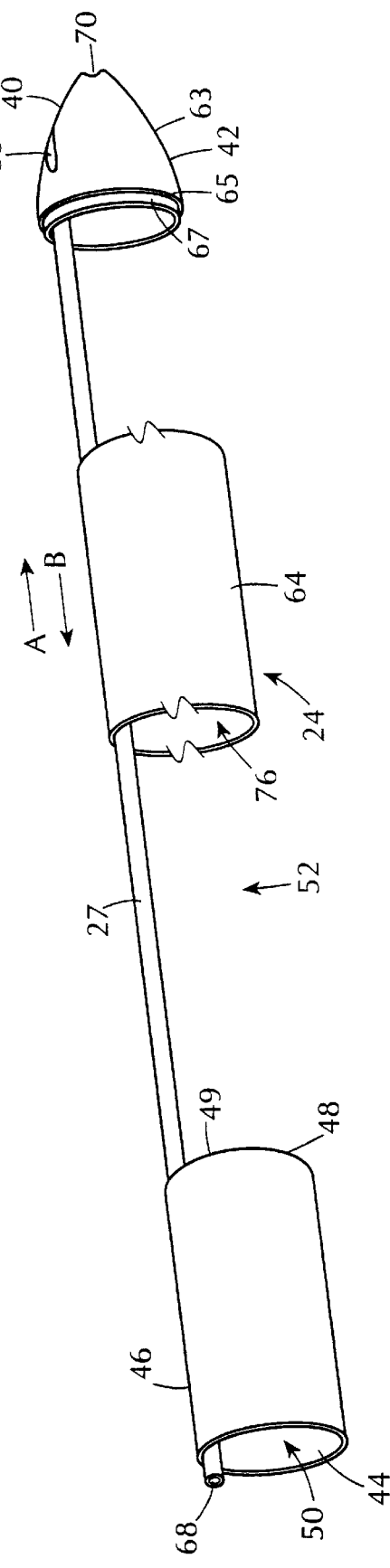

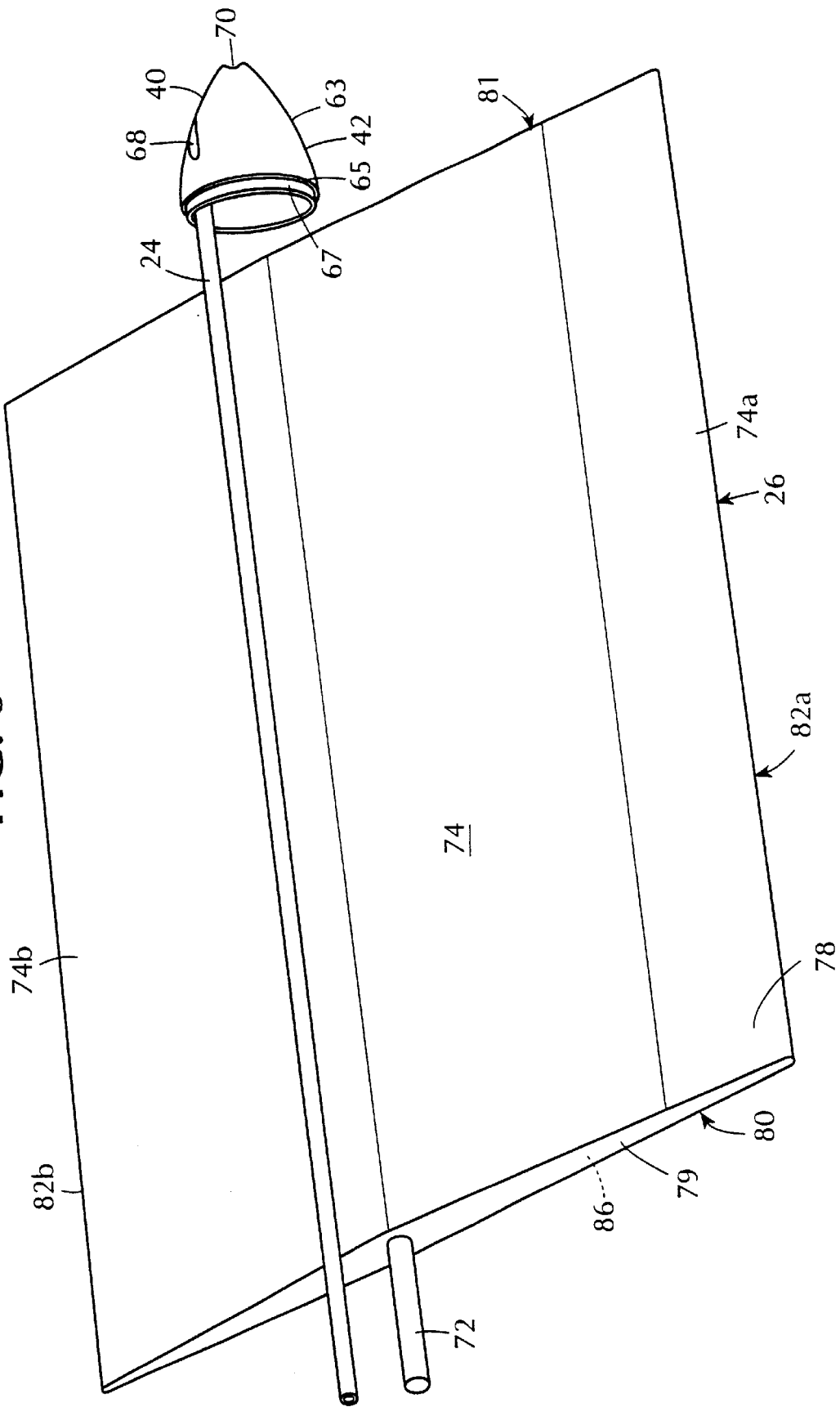

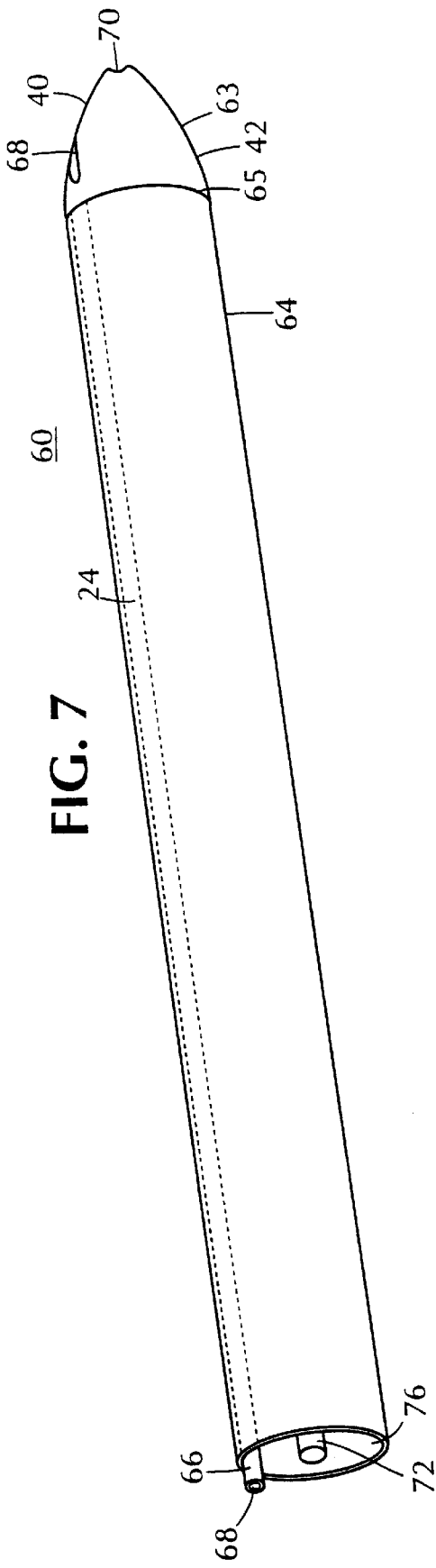
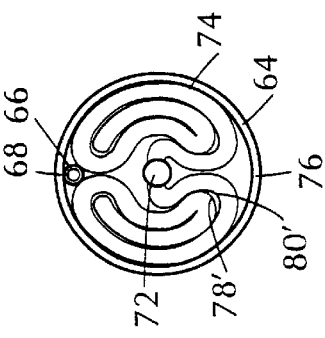
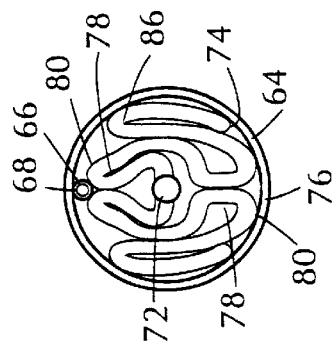
FIG. 7
FIG. 10
FIG. 9

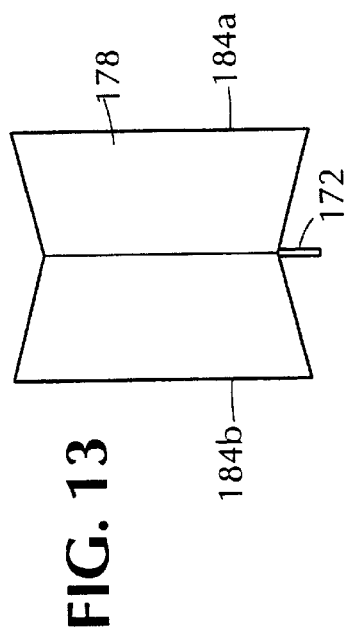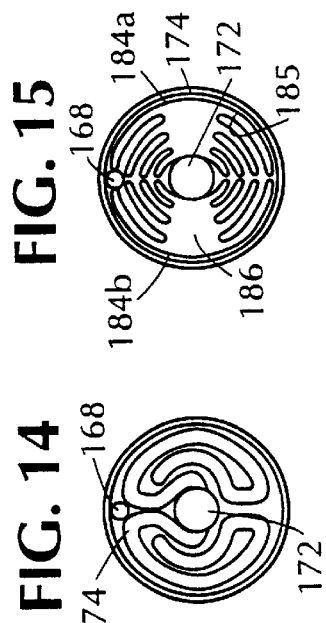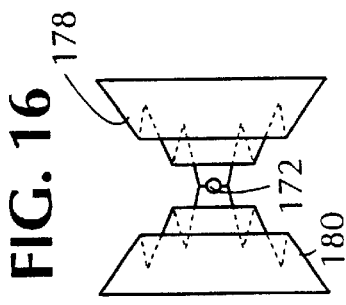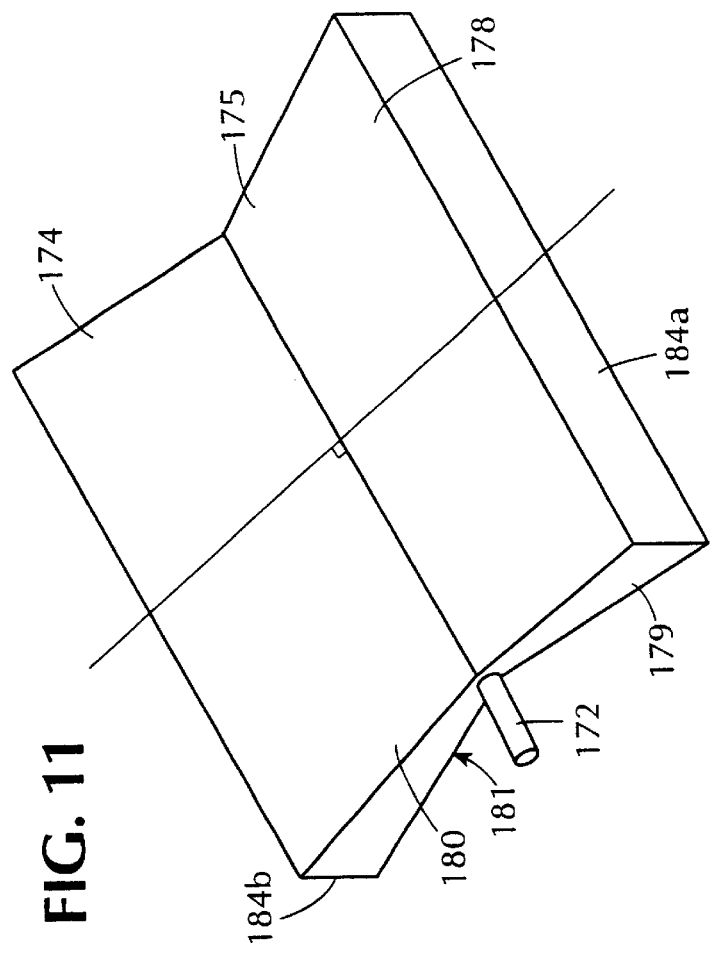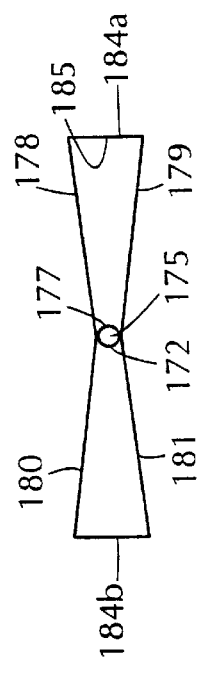

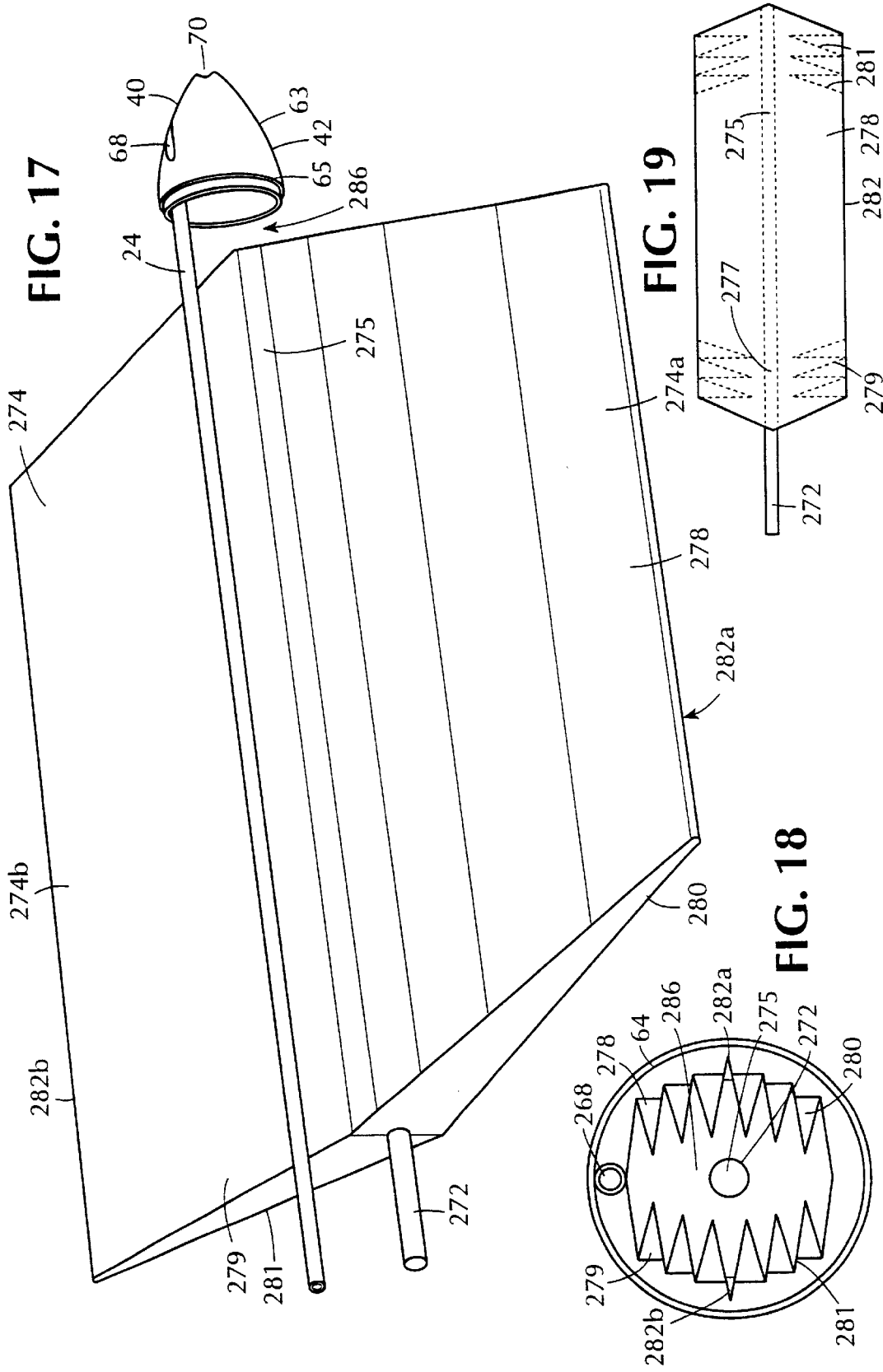

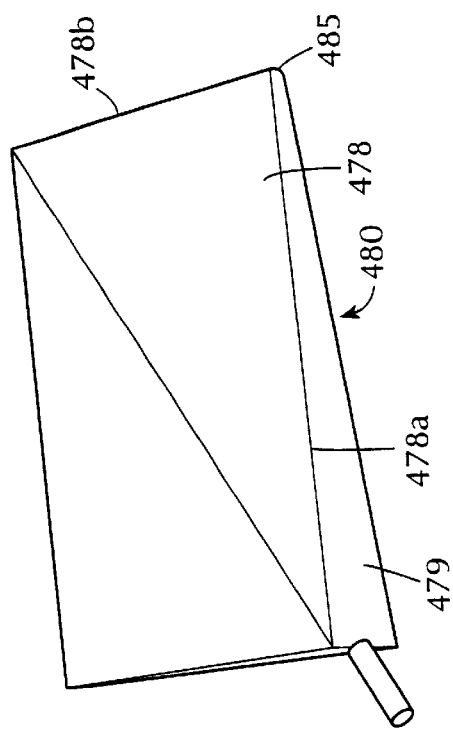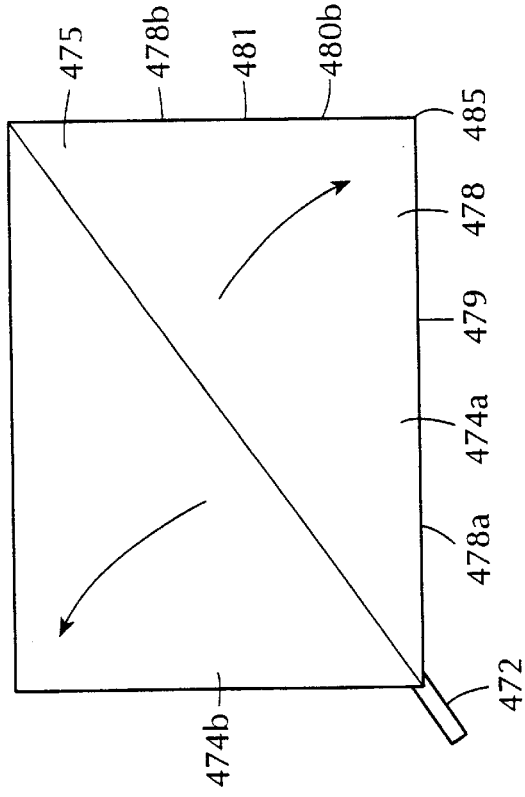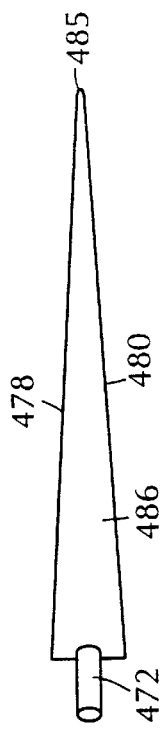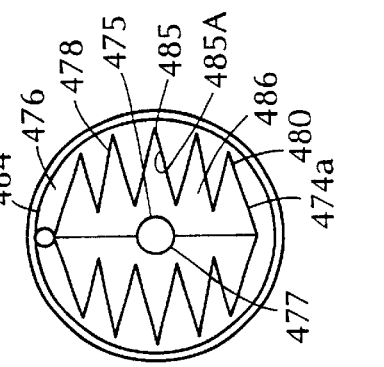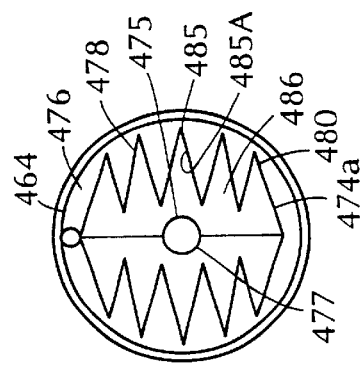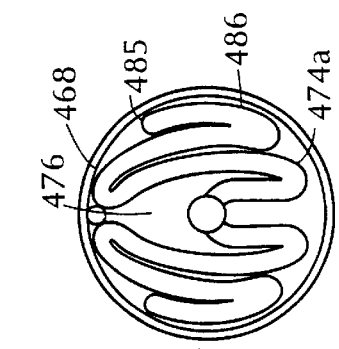

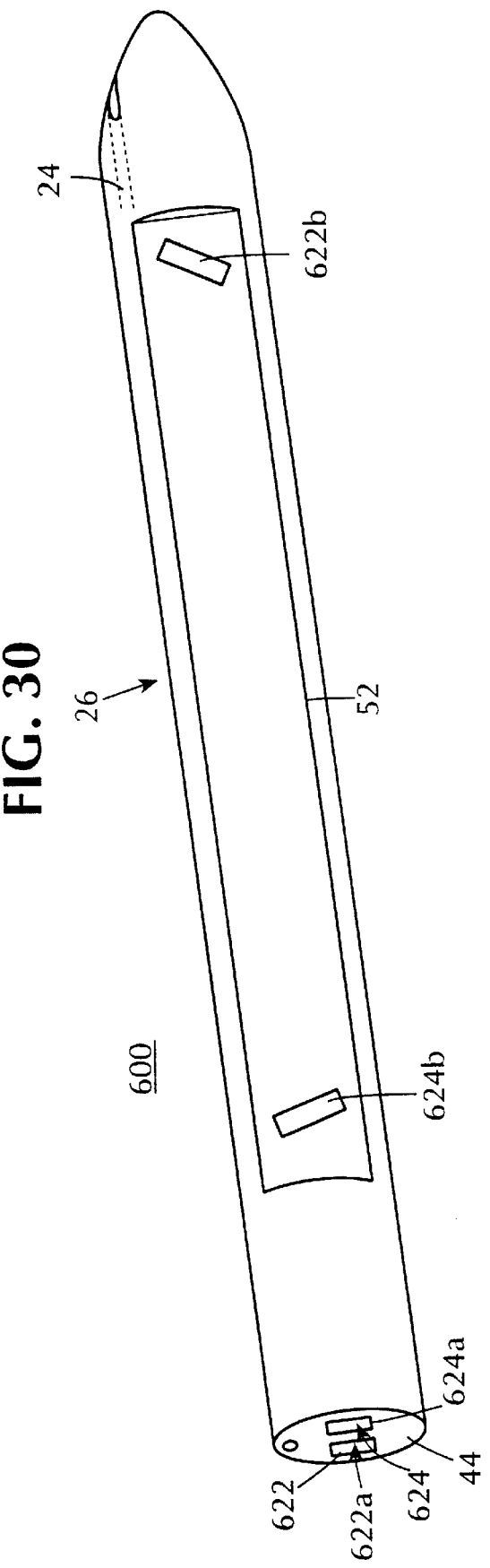

FIG. 31 FIG. 32
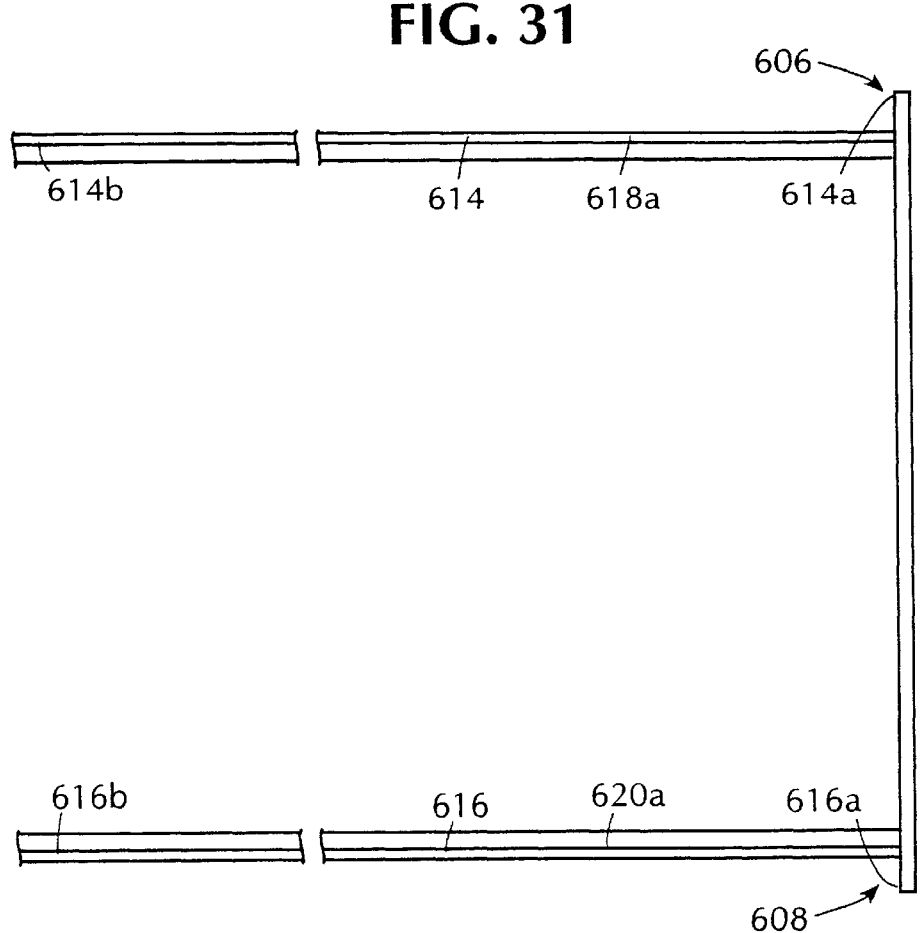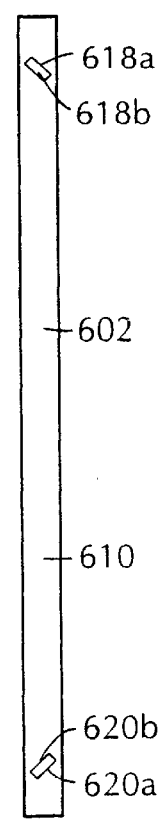
FIG. 33
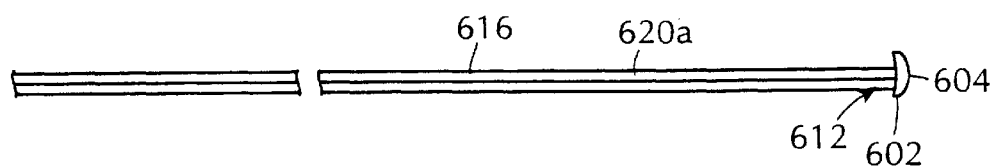

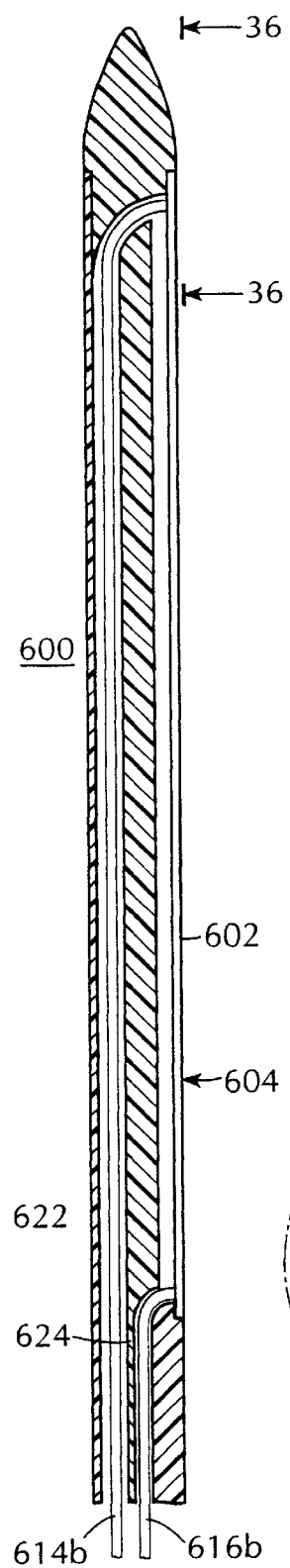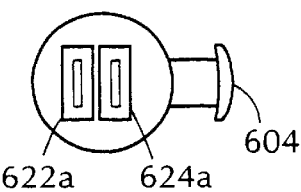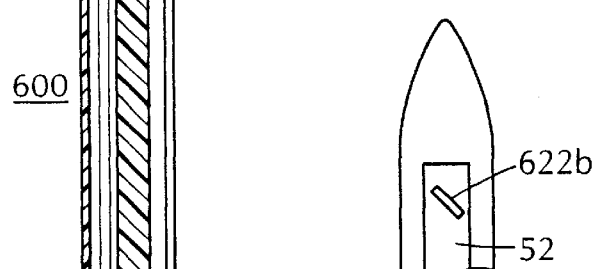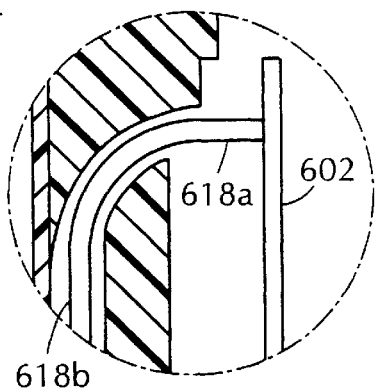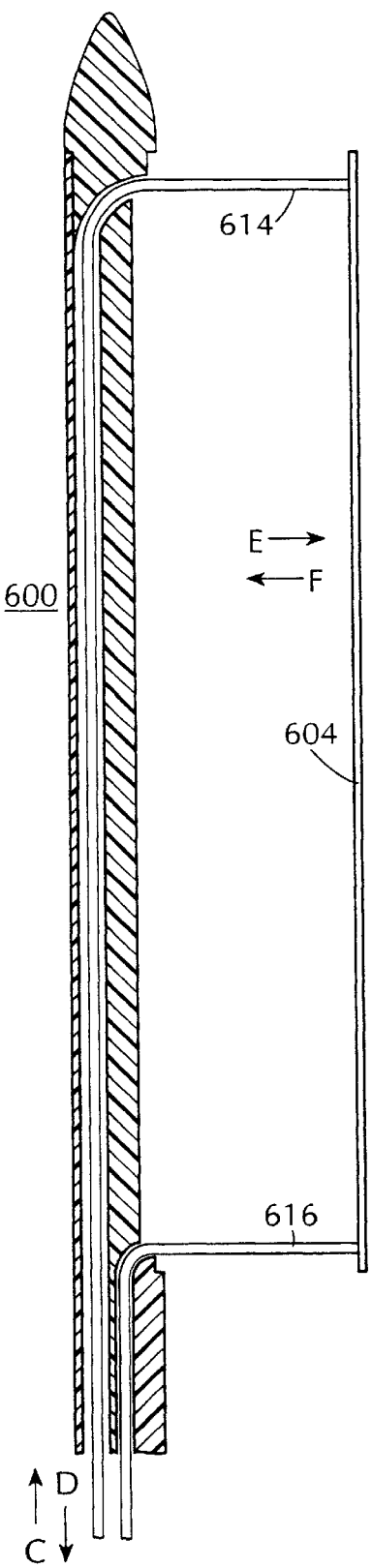

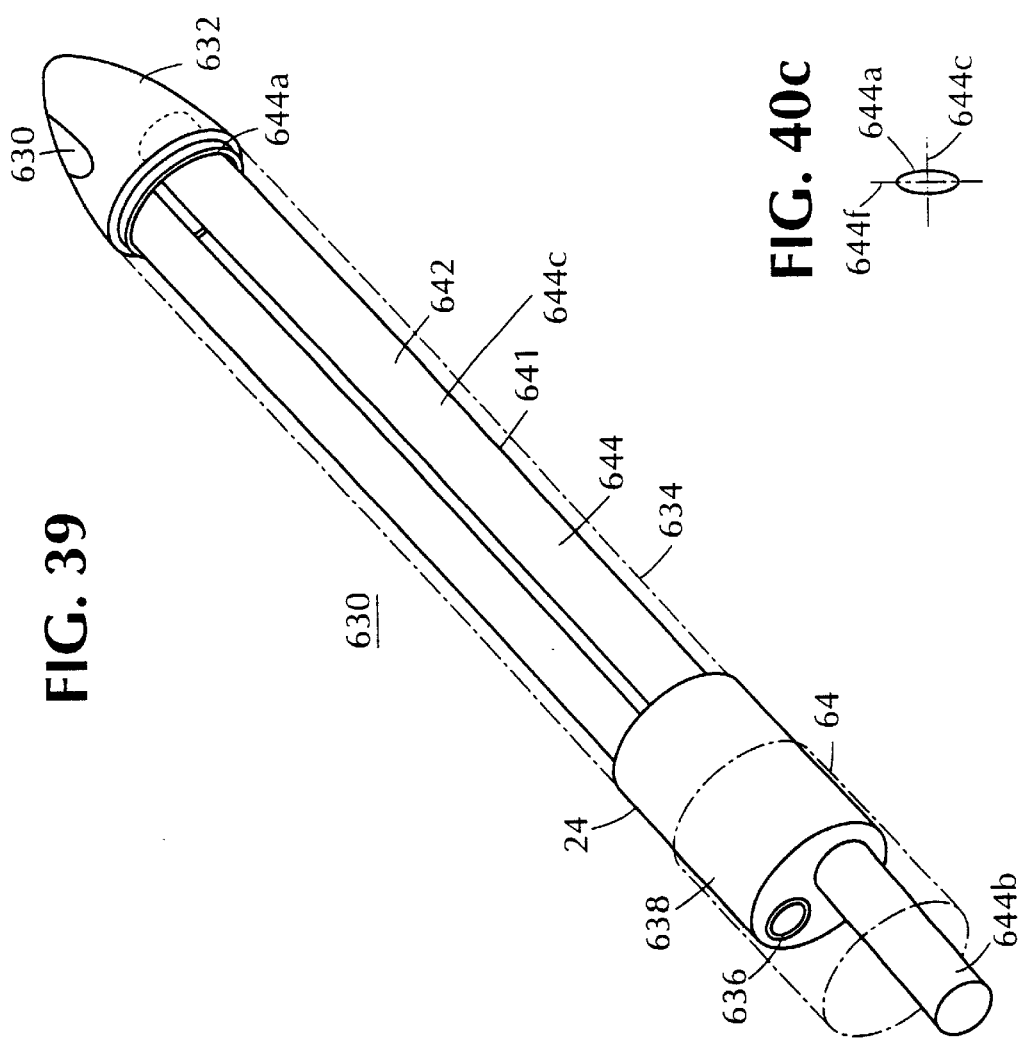

FIG. 46
FIG. 47
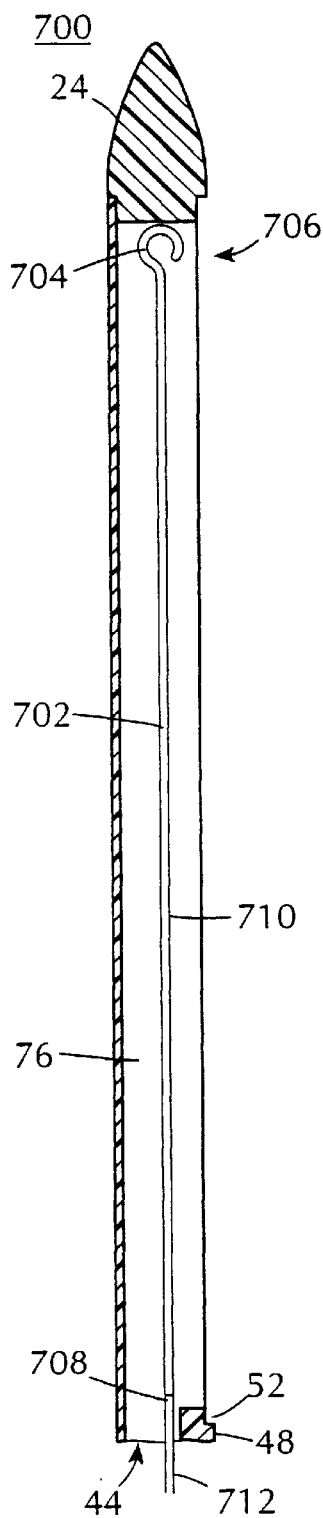
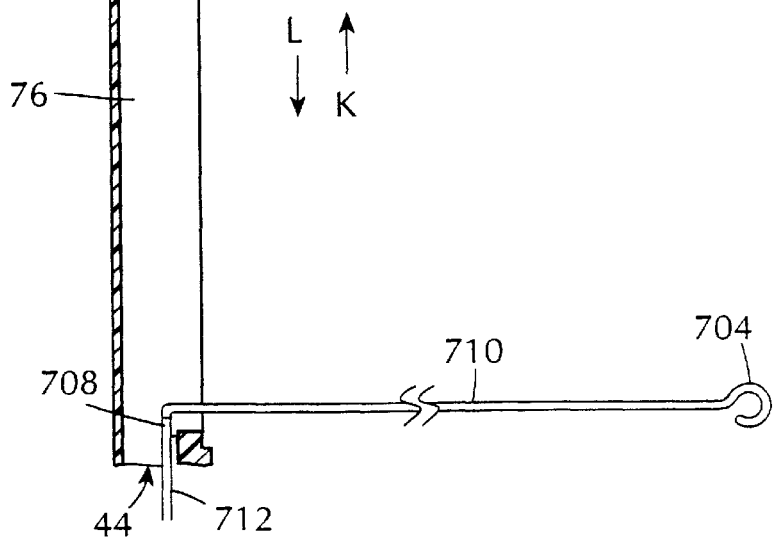

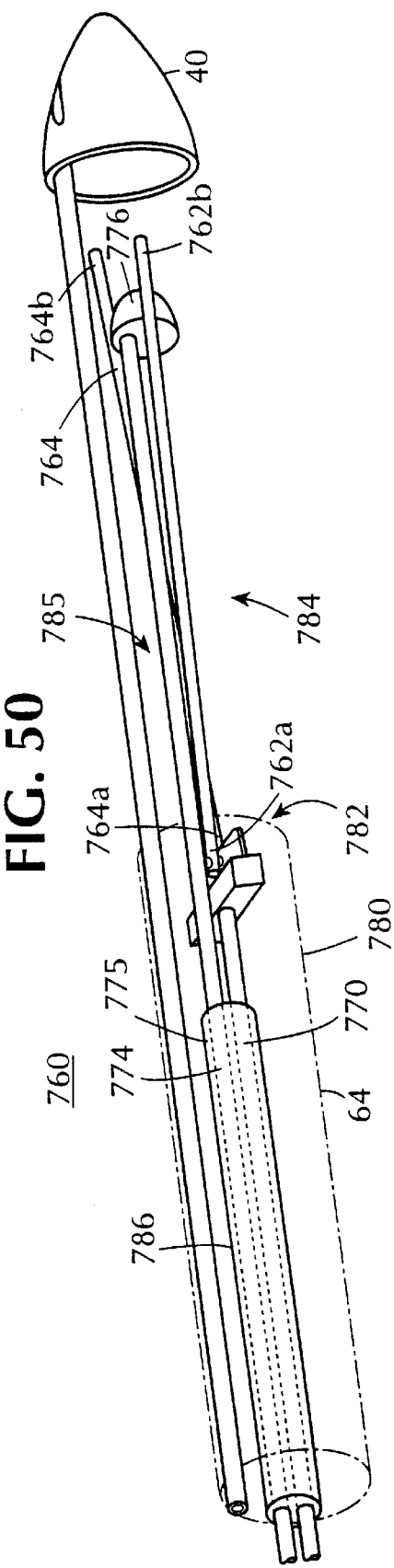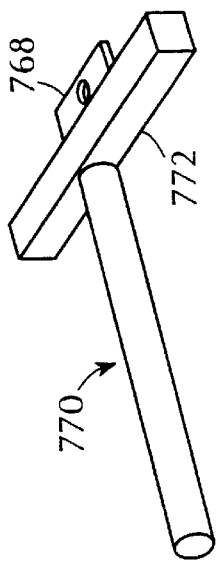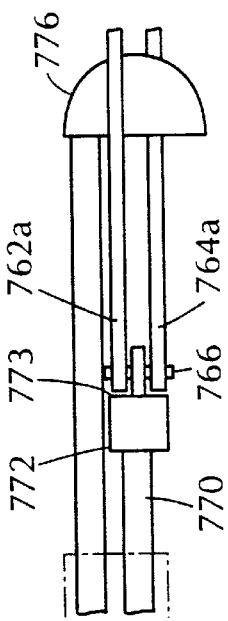
FIG. 50
FIG. 52
FIG. 51

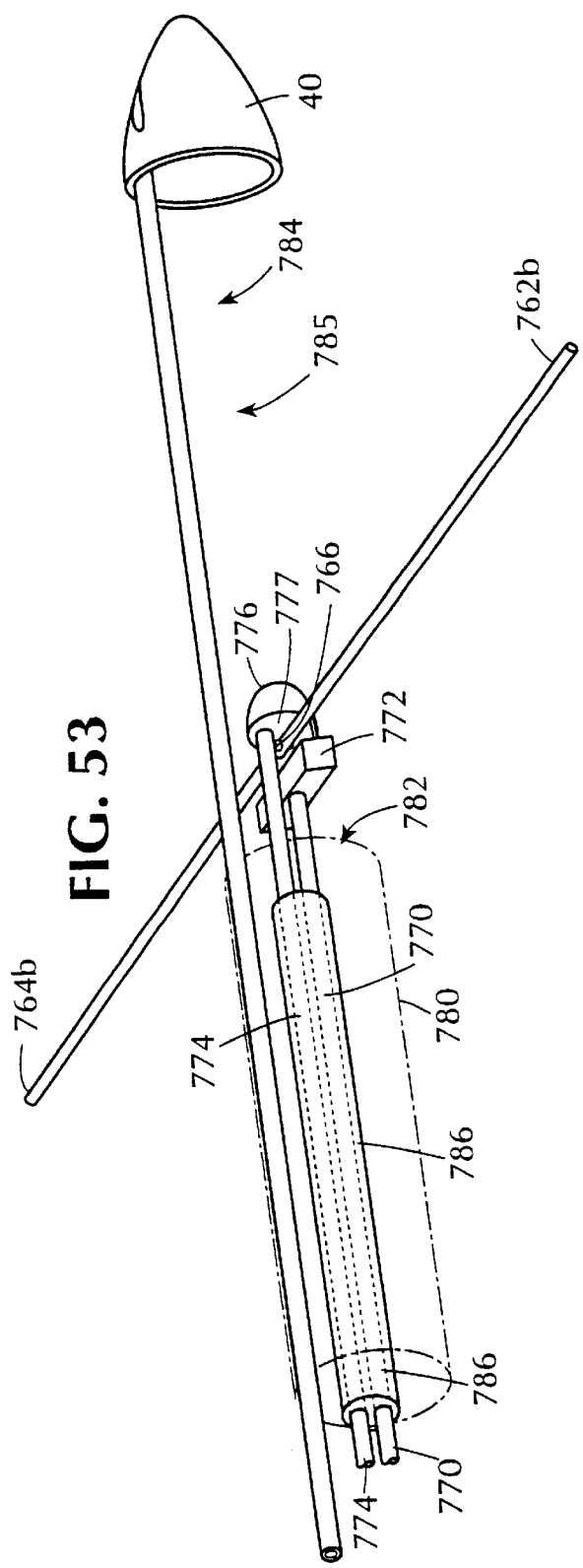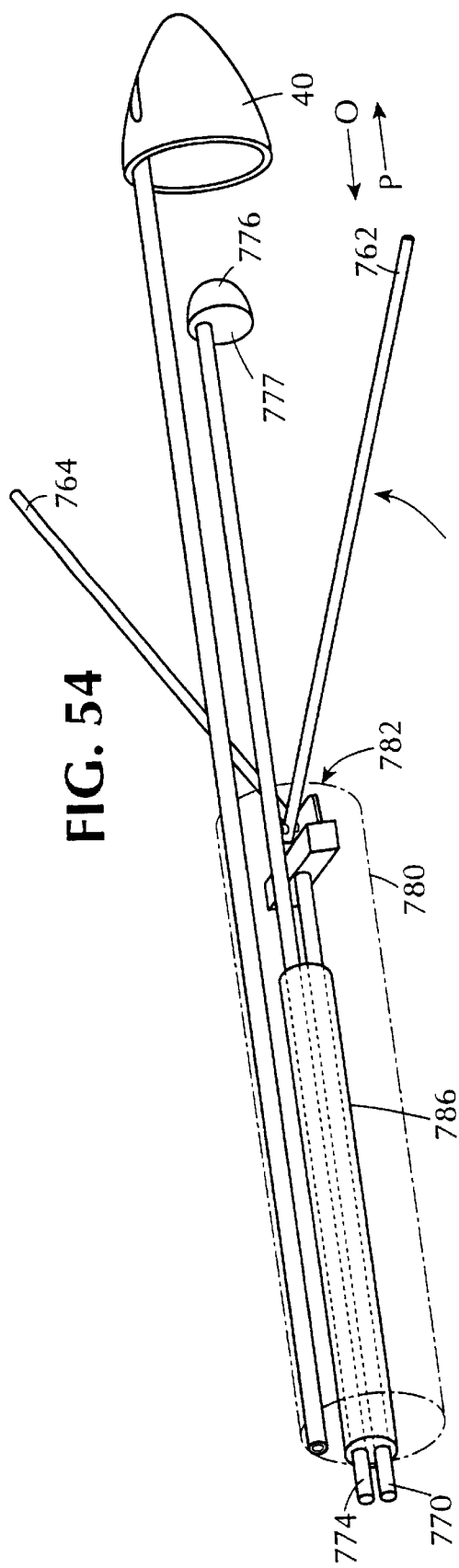
FIG. 53
FIG. 54

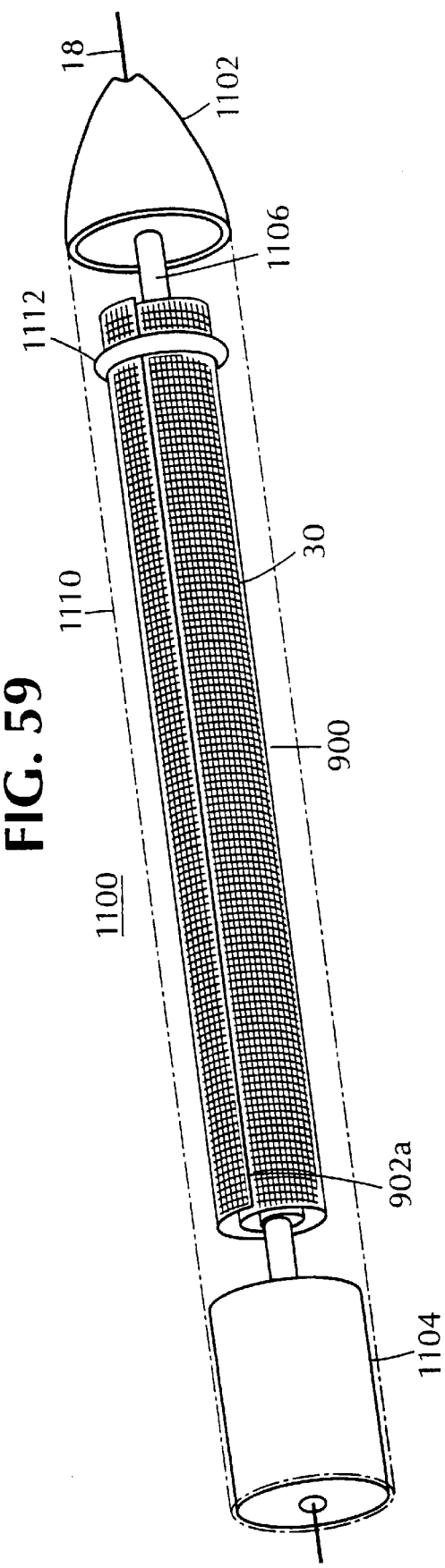
FIG. 59
FIG. 60
FIG. 61

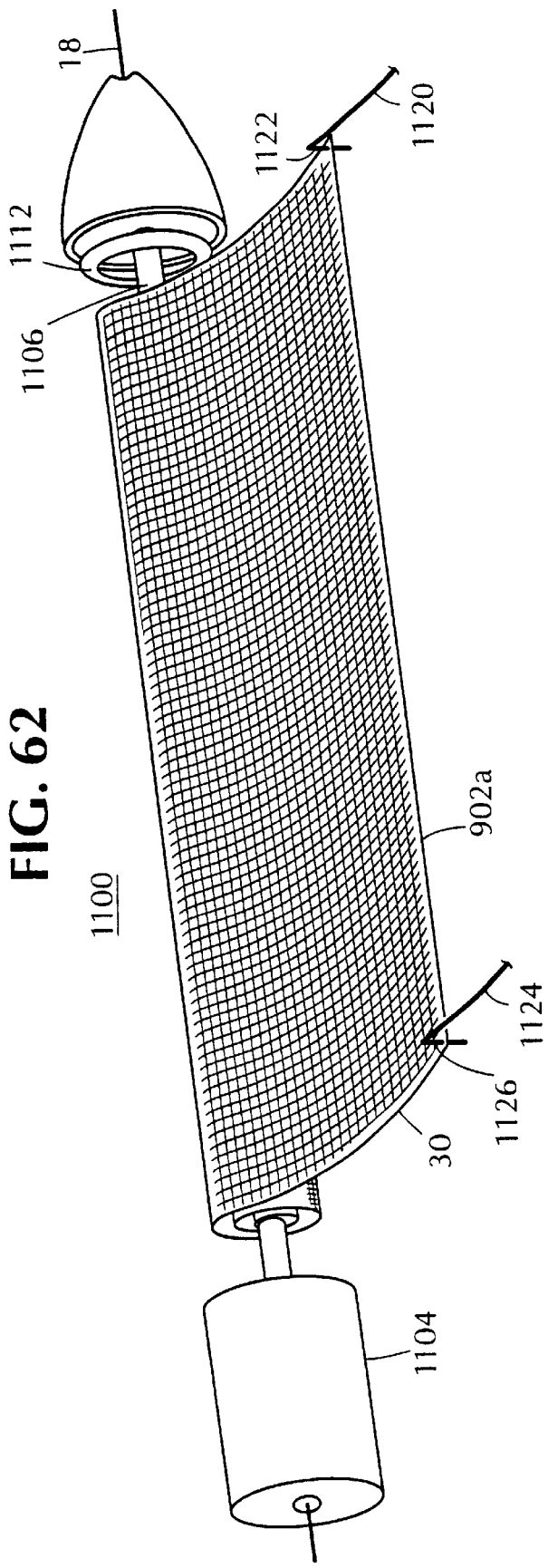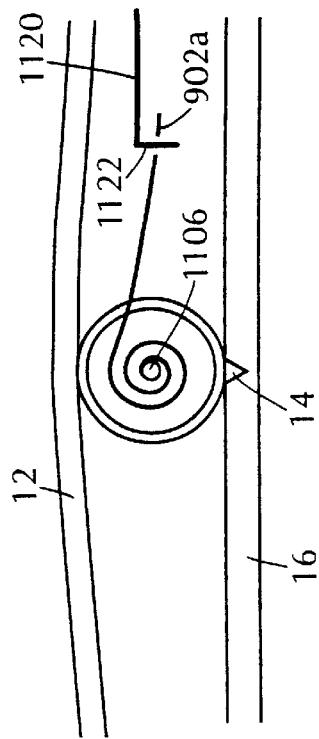

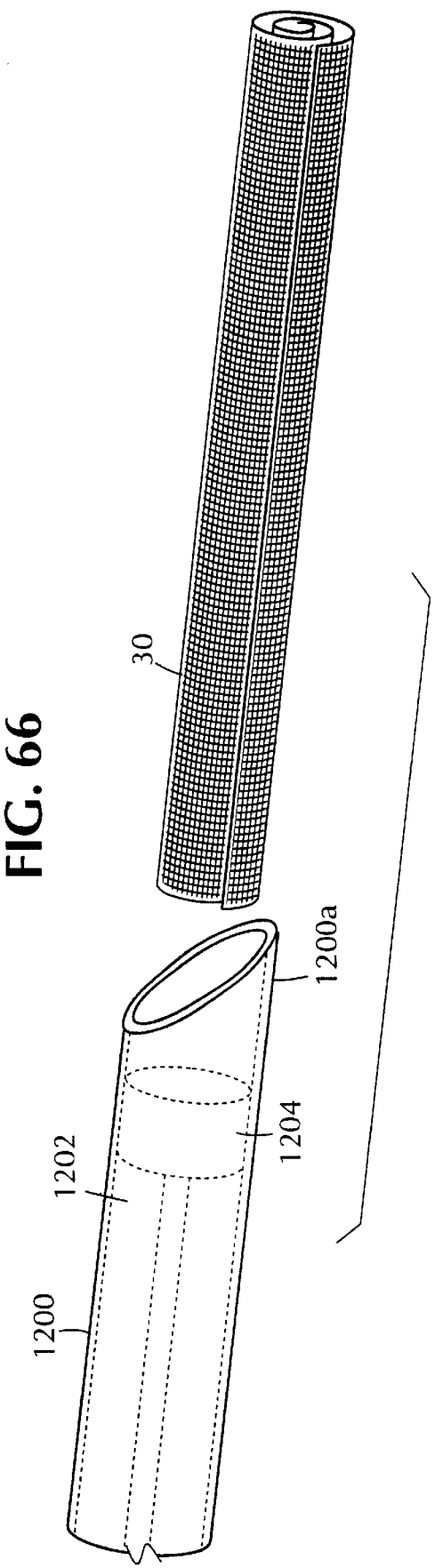

NEEDLE HERNIORRHAPHY DEVICES

This application is a divisional of U.S. Ser. No. 09/175,169, filed Oct. 20, 1998, now U.S. Pat. No. 6,099,518.

FIELD OF THE INVENTION

The present invention relates generally to methods and devices used to form an operating cavity between adjacent tissue layers of a patient. More specifically, the present invention relates to devices which may be percutaneously inserted into the body through a small diameter cannula and expanded between adjacent layers of tissue to provide an operating cavity in registry with an operating area and to provide a prosthesis to facilitate, for example, groin herniorrhaphy.

BACKGROUND OF THE INVENTION

Groin herniorrhaphy is among the oldest and most common surgical procedures performed. Unfortunately, the average operative result is beset by a period of discomfort with resultant disability. Techniques have been developed, such as laparoscopic herniorrhaphy, with the intent to reduce morbidity and recurrence rates. Most trials, however, have noted only a moderate improvement in the pain and disability associated with the procedure. Further, the added cost of equipment, the need for general anesthesia, and the additional operating room time required for this procedure indicates that it is less than ideal. There continues to be a need in general surgery for a procedure that can effectively address all the considerations of cost, disability, and hernia recurrence for patients with an inguinal hernia.

Failure of the transversalis fascia to retain the peritoneum from penetrating the myopectineal orifice is the fundamental cause of all groin hernias. Historically, hernias were repaired by stretching the transversus abdominis tendon across the myopectineal orifice and suturing it to the inguinal ligament. This technique and its current modifications rely upon the surgical approximations of edges of the defect to cover the myopectineal orifice. Such a technique, however, results in a distortion of the groin anatomy which creates stress on both the suture upon which the hernia repair is dependent and on the tissue planes that have already demonstrated their inherent weakness by the presence of a hernia. It is believed that the tension placed on the suture line as a result of the unnatural approximation of the tissues leads to recurrence, especially early recurrence.

A relatively modern technique to effect hernia repair is to place a prosthetic mesh over the myopectineal orifice. This technique enlists the intra-abdominal pressure to secure the inlayed prosthesis to the pelvic floor rather than allowing it to act as a factor in recurrence of the hernia. After mesh placement, the peritoneum becomes nondistensible, so there is no need for hernia defect closure. An effective modification of this technique is to place a polypropylene mesh on the outside of the myopectineal orifice. The prosthesis is sutured to the adjacent tissues with a minimum of tension. This repair has proven effective in preventing both short- and long-term recurrence. In addition, the pain associated with this operation is less than with other open operations. Its single disadvantage is the required division of tissue to gain access. The operation is commonly performed under local anesthesia with sedation. Hospitalization is avoided and most patients return to work as rapidly as those experiencing the laparoscopic preperitoneal herniorrhaphy.

Several mechanisms of hernia recurrence have been identified, such as the use of an inadequately-sized prosthesis so that the entire myopectineal orifice is not covered. Related to this concept of an inadequately-sized mesh is the possibility of inadequate overlap. It is felt that all defects should be overlapped by at least 2 cm if the mesh is stapled and by 3 cm or more if not stapled. For example, the myopectineal orifice measures approximately 10 cm×8 cm in an adult so a 16 cm×14 cm mesh is required.

While the placement of a prosthetic mesh in the preperitoneal space is currently performed with either a laparoscopic or an open technique, it is desirable to perform the procedure by placing small needle cannulas in the groin to dissect the preperitoneal space. Visualization would be obtained with a 2 mm laparoscope placed through one of the cannulas. The hernia sac would be dissected free and ligated. A prosthetic mesh would thereafter be placed to reinforce the transversalis fascia The patient would have reduced pain and disability as currently is associated with the procedure. In addition, the need for general anesthesia could be eliminated.

Such a needle herniorrhaphy technique requires a device for creating an operating space in registry with the myopectineal orifice. The device should be insertable through the cannulus of a needle. The device should further be either retrievable through the cannulus of the needle after creating the operating space or biodegradable so that it may be left in place over the herniated region.

Such a needle herniorrhaphy technique also requires a prosthesis employing a thin surgical support mesh that may be rolled or folded and thereafter inserted within the cannulus of a needle. The mesh should also be non-linting, fray resistant, and ravel resistant The mesh must be sufficiently porous to allow for tissue growth through the graft after implantation. The healing tissue grows through porous openings in the implanted mesh, thereby assimilating the mesh and adding structural integrity to the tissue.

The mesh is desirably self-opening upon emplacement over the myopectineal orifice. The mechanism for self-opening for the prosthesis must be reliable and should further provide suitable rigidity to the prosthesis in an open configuration, without unduly interfering with the anatomical members in the vicinity of the myopectineal orifice. Specifically, while the prosthesis should provide support to each side of the myopectineal orifice, the prosthesis should not interfere with, and risk closing of, the vas deferens. Additionally, the prosthesis should pose no risk of puncturing the peritoneurm so as to induce infection.

SUMMARY OF THE INVENTION

It is therefore an object of the invention to provide a device for creating an operating space in registry with the herniated region of a patient.

It is another object of the invention to provide a device for delivering a surgical prosthetic mesh to operating space in registry with a herniated region of a patient.

It is yet another object of the present invention to provide a device for performing herniorrhaphy having a relatively small diameter so as to minimize the need for general anesthesia.

It is still yet another object of the invention to provide a mechanism for separating adjacent tissue layers within a patient so as to provide an operating space.

It is even still another object of the present invention to provide a mechanism for separating adjacent tissue layers within a patient that may delivered through a small diameter cannula.

It is yet even another object of the present invention to provide a mechanism which may be delivered through a small diameter cannula that will both separate adjacent tissue layers and deliver a prosthetic mesh to the operating space being created.

In the efficient attainment of these and other objects, the present invention provides an instrument for creating an operating space in a body in the form of an elongate blunt-nose cannula having an elongate side wall defining an access aperture, an interior lumen, and an elongate aperture. The cannula is deliverable along a guidewire between a first and second tissue layer in a body. The instrument also includes a retractable outer protective sheath, a fluid delivery lumen communicating with a fluid source, and a hollow expandable tissue separating balloon including a first major surface and a second major surface. The first major surface is peripherally contiguous with the second major surface and together the first and second major surfaces define a fluid-tight balloon cavity therebetween. The balloon cavity communicates with the fluid delivery lumen and is expandable through the elongate aperture of the cannula body from a first contracted configuration confined within the cannula body to a second expanded configuration extending through the elongate window. Expansion of the balloon thereby forces apart the adjacent first and second tissue layers so as to form the operating cavity.

The delivery cannula of the present invention is less than about 10 millimeters although diameters of between about 5 millimeters and 2 millimeters is desirable. Therefore the tissue separating balloons of the present invention are designed to have shapes which may be rolled, folded, or collapsed within a small diameter lumen. For example, several of the balloons of the present invention provide major surfaces with opposed tapering edges. The major surfaces of these balloons may be pleated, or alternately folded upon themselves, so as to effectively telescope outwardly from the stored configuration upon balloon inflation. The tapering edges minimize bunching up of the balloon material and thereby minimize the required mean diameter of the delivery cannula.

The cannula and balloon of the present invention are contemplated as providing for expansion of the balloon towards one side of the cannula. The cannula and balloon of the present invention are also contemplated as providing for expansion of the balloon towards two opposing sides of the cannula so as to centrally locate the guidewire in registry with the operating site being treated. Additionally, the balloon of the present invention may be formed to expand symmetrically about the cannula or in a longitudinally reversed symmetry so as to position the guidewire in registry with a diagonal axis of the operating space being treated.

Alternatively, the present invention provides a boundary balloon in that the balloon takes the form of a tubular wall having a substantially rectangular frame shape. In its fully inflated state the balloon is positioned only at the periphery of the created operating space. As it is not necessary to maintain the tissue layers apart once separated, a frame balloon provides for a maximum amount of space to be created for a given amount of balloon material. As less material is required to create an operating space, the diameter of the delivery cannula may be further reduced.

It is further contemplated that each of the balloons of the present invention may carry a porous surgical mesh so that upon expansion of the balloon the mesh will be unfurled over the operating site. The mesh may be detachable from the balloon so that the balloon may be withdrawn from the operating space once the mesh is emplaced. It is also contemplated that the balloon of the present invention may itself be detached from the fluid delivery lumen of the cannula so that the balloon may be left within with the mesh in registry with the operating space. Such a detachable balloon would be desirably formed from a bioabsorbable material.

In order to further minimize the required diameter of the cannula, the present invention also contemplates a detachable balloon having a major surface formed from a plugged porous surgical mesh. That is, the pores of the surgical mesh are plugged or filled so as to maintain the fluid integrity of the balloon during expansion by internal fluid pressure. However, the material used to fill the pores of the mesh will also be bioabsorbable so that as the filler material is absorbed by the body, the pores will be exposed so as to permit new tissue ingrowth therethrough. The remainder of the balloon is also formed from a bioabsorbable material. This balloon obviates the need for providing a major surface of the balloon simply to support a prosthetic mesh thereon and thereby decreases the required stored volume of the balloon and diameter of the delivery cannula.

The present invention also contemplates a device for creating an operating cavity in a mammal between two adjoining layers of tissue adjacent to an operating site on one of the tissue layers. The device includes an elongate hollow cannula defining an elongate interior lumen, an access port communicating with the interior lumen and accessible outside the body of a patient, and an elongate aperture also communicating with the interior lumen and accessible to the deployment area. The device includes a blunt nose for introducing the device into the body, and a guidewire-deliverable dissecting member which is deliverable within the interior lumen of the cannula to a deployment area adjacent to the operating site.

In one embodiment of the present invention, the cannula supports a dissecting member including an elongate dissecting tip transversely extendable from the elongate aperture of the dissecting member. The dissecting member further includes actuator means for retractably extending the dissecting tip from the dissecting member to separate layers of tissue adjacent the operating area to form the operating cavity. The dissecting tip is a substantially rigid member which will exhibit a minimum of deflection as it is extended between to the adjacent tissue layers so as to separate same.

The actuator means is desirably a pair of elongate push rods which extend and retract normally to the dissecting member and which may bend to negotiate a ninety degree turn so as to extend longitudinally through the cannula. The cannula desirably provides exclusive passageways for accommodating each push rod. The passageways are desirably conformally shaped to the outside surfaces of the push rods, which are desirably both rectangular. In order to minimize the buckling of the push rods as the dissecting tip is extended, the cannula passageways desirably impart a twist to the push rods so that deflection of the push rods will be directed against the adjacent tissue layers and not simply therebetween. A surgeon may apply light pressure from the outside of the patient to counteract the buckling of the push rods. Once the dissecting tip has been pushed to its maximum limit, the push rods may be retracted back through the cannula. If desired, especially where it is beneficial to centrally locate the guidewire within the operating space, the operator may rotate the cannula about the guidewire and extend the dissecting tip in the transversely-opposite direction so as to provide a larger operating cavity.

The present invention also contemplates providing a flexible wire within the cannula that has one end anchored to the blunt nose and the opposed free end extending through the lumen exterior of the patient. This embodiment further provides an elongate cannula window opening in one transverse direction towards the non-separated tissue layers. The flexible wire may be extended towards the blunt nose so as to buckle the wire outwardly through the cannula window so as to be forced between and to separate the adjacent tissue layers in order to form the operating cavity. The flexible wire may be formed having a cross-sectional shape which favors buckling towards the cannula window. The flexible wire may also have various projections on the surface thereof which facilitate tissue separation. Additionally, the cannula may provide a longitudinally centrally located protrusion formed on the cannula wall in facing opposition to the window and adjacent the flexible wire so as to instigate buckling of the wire towards the window. After retracting the flexible wire back into through the window, the operator may rotate the cannula about the guidewire until the window faces in the opposite transverse direction as before so as to provide an enlarged operating cavity with the guidewire centrally located in registry therewith. An alternate embodiment of this device provides a second elongate window communicating to the opposite direction as the first window and a second flexible wire similarly anchored to the blunt nose for extension through the second window so as to simultaneously form the enlarged operating space to either side of the guidewire.

The present invention further contemplates providing a tissue dissecting device within the cannula which is formed from a shape memory material and which has been deformed to be deliverable within the cannula to a location between two adjacent tissue layers in the body. The shape memory material is desirably activated by body temperature to assume a configuration where a tissue separating blade extends out through the cannula window and thereby separate the adjacent tissue layers. The extended blade is desirably longitudinally movable along the length of the window to create the desired operating space. The blade is desirably connected to an actuating rod extending through the lumen of the cannula outside the patient. An alternate embodiment of this device provides a second tissue separating blade formed from a shape memory material to extend in the opposite transverse direction so that the guidewire will be centrally located within the resulting operating cavity.

An even further embodiment of the present invention provides a pair of oppositely-extendable elongate blades having one end pivotally connected to a pivot pin carried at one end of an elongate support wire adjacent a blade stop surface. The opposite ends of the blades are transversely separated by a deployment wedge which is supported at the end of an elongate actuation wire. The deployment wedge includes a planar face in facing opposition to the blade stop surface. The actuation wire is extendable and retractable along the support wire. Retraction of the actuation wire retracts the deployment wedge which forces the blades to pivot outwardly from the cannula to separate the adjacent tissue layers. The blades transversely extend from the cannula when the planar face of the deployment wedge pins the blades against the blade stop surface. The operator may then axially extend both the actuation wire and the support wire so as to extend the tissue separating blades along the length of the cannula window and thereby form the operating cavity.

The present invention even further provides a device for delivering a surgical prosthetic mesh to a previously-formed operating space. The mesh delivery device includes an elongate cannula body having an elongate cannula cylindrical wall of a first outside diameter supporting an elongate cylindrical guidewire conduit having a second smaller outside diameter and an interior passageway for accommodating a guidewire. The distal end of the guidewire conduit supports a blunt nose including a cylindrical rim having the same diameter as the cylindrical cannula wall. The device defines a cylindrical cannula window, and a cylindrical mesh delivery area about the guidewire conduit, between the cannula cylindrical wall and the blunt nose. An elongate retractable sheath extends along the outside of the cylindrical cannula wall to the surface of the rim of the blunt nose. A prosthetic mesh is deployably wrapped about the guidewire conduit. The mesh may be wrapped by placing one edge of the mesh along the guidewire conduit and then furling the mesh about thereabout. Once the cannula is positioned within the operating cavity, the sheath is retracted to expose the prosthetic mesh. The free edge of the mesh may be grasped and transversely pulled to deploy the mesh within the operating space.

Alternatively, the mesh may be longitudinally folded so that the opposed edges of the mesh are brought towards each other. The crease is then place along the guidewire conduit. Furling the mesh about the guidewire conduit provides the opposed edges to either side of the guidewire conduit. The opposed edges may be simultaneously pulled in opposite directions to deploy the mesh within the operating space. This alternative delivery configuration for the mesh is advantageously employed when the guidewire is centrally located within the operating cavity.

The present invention also provides methods for employing the devices of the present invention.

The present invention will be more readily appreciated in a reading of the "Detailed Description of the Preferred Embodiments" with reference to the drawings.

BRIEF DESCRIPTION OF THE DRAWINGS

FIG. 4 depicts a cannula for delivering a tissue separating device of the present invention.

FIG. 5 is a partial cut away view of the cannula of FIG. 4.

FIG. 7 depicts a cannula for delivering the tissue separating balloon of FIG. 6.

FIG. 9 is a cross-sectional view of the cannula in FIG. 7 showing one delivery configuration for the tissue separating balloon.

FIG. 10 is cross-section of the cannula of FIG. 7 depicting an alternate delivery configuration for the tissue separating balloon carried therein.

FIGS. 11, 12 and 13 depict a second embodiment for a tissue separating balloon of the present invention.

FIGS. 14 and 15 depict alternate delivery configurations for the tissue separating balloon of FIGS. 11–13.

FIG. 16 is a schematic representation of the tissue separating balloon of FIGS. 11–13 when delivered as shown in FIG. 15.

FIG. 17 depicts yet another tissue separating balloon of the present invention.

FIG. 18 is a cross-sectional view of the tissue separating balloon of FIG. 17 as configured within a delivery cannula of the present invention.

FIG. 19 is a top view of one wing of the tissue separating balloon of FIG. 17 being folded into a pleated delivery configuration.

FIGS. 24 and 25 depict even still another tissue separating balloon of the present invention.

FIG. 26 provides an elevational view of one wing of the tissue separating balloon of FIGS. 24 and 25 in the inflated configuration.

FIG. 27 is a cross-sectional view of the tissue separating balloon of FIGS. 24 and 25 folded in a serpentine within a delivery cannula.

FIG. 28 is a cross-sectional view of a tissue separating balloon of FIGS. 24 and 25 in a rolled configuration within a delivery cannula of the present invention.

FIG. 29 is a cross-sectional view of a tissue separating balloon of FIGS. 24 and 25 in a pleated configuration within a delivery cannula of the present invention.

FIGS. 30–38 depict an alternate embodiment of a tissue separating device of the present invention.

FIGS. 39–43 depict yet another alternate embodiment of a tissue separating device of the present invention.

FIGS. 46 and 47 depict a tissue separating device of the present invention employing a tissue separating blade formed from a shape memory material.

FIGS. 50–54 depict a further tissue separating device of the present invention employing an extendable wire tissue-separating means.

FIGS. 59–65 depict a prosthesis delivery device of the present invention and the use thereof.

FIG. 66 depicts a thin mesh being expelled from a small diameter cannula in accordance with the present invention.

DETAILED DESCRIPTION OF THE PREFERRED EMBODIMENTS

The present invention relates to devices and methods for performing hernia repair. The present invention provides for repairing hernias using needle herniorrhaphy techniques which may be performed using only a local anesthesia on an out-patient basis.

Figure 1:
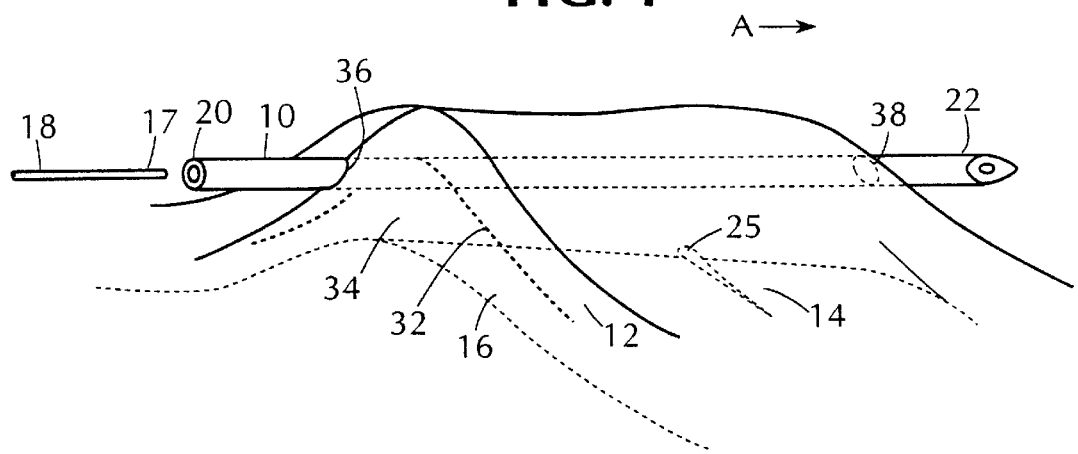
FIG. 1 depicts the insertion of a guidewire in registry with a herniated region according to the present invention.
Figure 2:
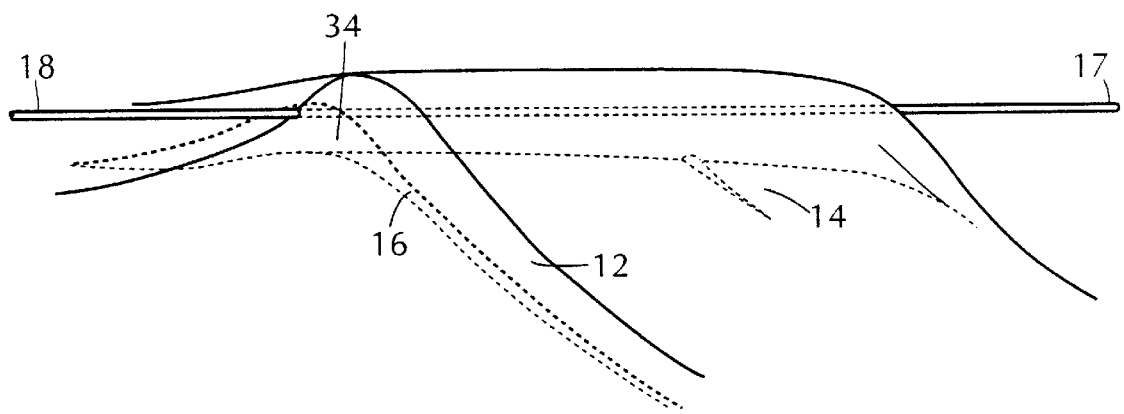
FIG. 2 depicts a guidewire positioned in registry with a herniated region.
Figure 3:
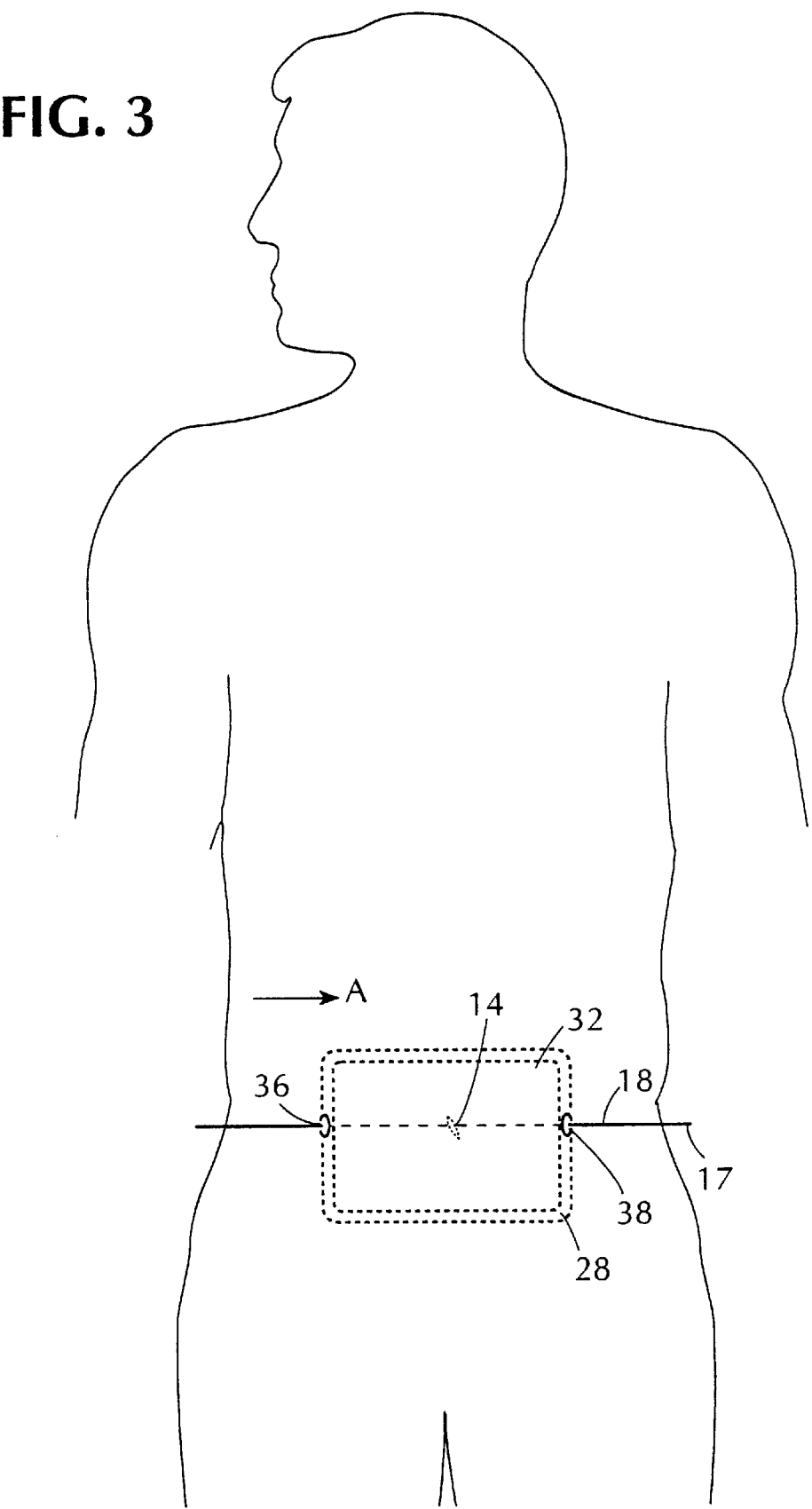
FIG. 3 is an elevational schematic of a guidewire inserted in registry with a herniated region within a patient.

Needle herniorrhaphy is a laparoscopic-like method of repairing a hernia utilizing a trocar on the order of about five to ten millimeters in diameter although it is contemplated that a trocar of about two millimeters in diameter may also be utilized. Referring to FIGS. 1–3, a method employing the devices of the present invention inserts an elongate hollow trocar 10 through the abdominal wall 12 of a patient from one side of the herniated region 14, passes the trocar 10 over the peritoneum 16 above the herniated region 14, and out through the abdominal wall 12 of the patient opposite the herniated region 14 from where the trocar 10 was inserted. A first end 17 of a guidewire 18 is inserted through a first end 20 of the trocar 10 and out the second end 22 of the trocar 20 so as to extend completely through the trocar 10. Trocar 10 is then pulled over first end 17 of guidewire 18 until out of the patient and then removed from the guidewire 18 altogether. An elongate cannula 24 for providing a tissue dissection device 26 of the present invention is then threaded over one end of guidewire 18 and inserted though abdominal wall 12 until positioned adjacent the peritoneum 16 over the herniated region 14. The tissue dissection device 26 is operated to separate the abdominal wall 12 from the peritoneum 16 about the herniated region 14 to create an operating space 28 in registry therewith. Operating space 28 is desirably formed in registry with the myopectineal orifice 32 and extends approximately 2 to 3 centimeters beyond the perimeter thereof. As will be discussed hereinbelow, after operating space 28 has been created, the hernia sac 25 may be ligated and a prosthetic mesh 30 may be deployed over the herniated region 14 of the peritoneum 16 so as to induce tissue growth through the mesh 30 and to effect repair of the hernia.

The present invention provides several devices and methods for performing the steps of separating the abdominal wall from the peritoneum and for deploying a mesh over the herniated region of the peritoneum. The devices and methods for each step may be combined to form a composite device or devices for performing the herniorrhaphy. These devices and methods will be described in greater detail hereinbelow.

1. Guidewire Emplacement

With reference to FIG. 1, a method for treating an inguinal hernia includes running a guidewire 18 above the myopectineal orifice 32. Guidewire 18 may be positioned by pinching the abdominal wall 12 adjacent the myopectineal orifice 32 to isolate an exploitable junction 33 therebetween the peritoneum 16 and the abdominal wall 12. A penetration end 22 of an elongate hollow trocar 10 is then inserted through the abdominal wall 12, forming insertion puncture 36, until between the peritoneum 16 and the abdominal wall 12. Penetration end 22 is pushed between the peritoneum 16 and the abdominal wall 12 so as to pass over the region of the myopectineal orifice 32 where it then punctures through abdominal wall 12, forming exit puncture 38, to exit the body of the patient. Penetration end 22 may be formed having a relatively blunt shape so as to minimize the risk of scratching or puncturing the peritoneum 16 as it forms gap 34. Such shapes for blunt needles are well known in the art. Trocar 10 is formed of a suitable surgical material and desirably is formed having an outer diameter between 2 and 10 millimeters.

With trocar 10 now percutaneously transiting the body adjacent the herniated region 14, first end 17 of guidewire 18 is inserted through first end 20 of trocar 10 and therethrough and out of penetration end of trocar 22. Holding guidewire 18 stationary, trocar 10 is fully pulled through gap 25 over guidewire 18 in the direction of arrow A until clear of first end 17. Now guidewire 18 percutaneously transits the body over the herniated region 14 between insertion puncture 36 and exit puncture 38. Guidewire 18 is formed of a suitable surgical material as is known in the surgical arts and is desirably selected so as to minimize the risk of scratching or cutting the peritoneum.

2. Guidewire-Deliverable Cannula

With guidewire 18 now positioned proximal to herniated region 14, an elongate cannula 24, shown in FIGS. 4–5, may be delivered along guidewire 18 through insertion puncture 36 to a position within gap 34. Cannula 24 includes a blunt tip 40 at a first end 42, a cannula wall 48 at a second end 46, and an elongate guidewire conduit 27 extending therebetween. Cannula 24 is desirably formed of stainless steel when formed having a relatively small outside diameter. It is also contemplated that cannula 24 may be desirably formed of a suitable surgical plastic material when formed having a relatively larger outside diameter.

Cannula wall 48 defines an access aperture 44 at second end 46 and an interior passageway 50 extending towards blunt tip 40. The exterior of cannula 24 further includes an elongate hollow retractable sheath 64 extending from blunt tip 40 towards access aperture 44 a sufficient length so as to protrude from insertion aperture 36 when cannula 24 is positioned within gap 34. Sheath 64 covers a delivery cavity 76 extending from a distal rim 49 of cannula wall 49 to blunt tip 40. Cannula 24 further defines an elongate cannula window 52 extending between blunt tip 40 and distal rim 49 of cannula wall 48 and providing access to delivery cavity 76. Sheath 64 provides protective cover over cannula window 52 and delivery cavity 76 for delivery within gap 34.

Blunt tip 40 is further described as including an oblong nose body 62 having a leading surface 63 tapering from a transversely-oriented sheath-accommodating rim 65 towards an open tip 70. Nose body 62 also includes a cylindrical annulus 67 spaced across rim 65 from lead surface 63. Annulus 67 releasably adheres to the distal end 64a of retractable sheath 64. Once positioned within gap 34, the protruding end of sheath 64 may be pulled in the direction of arrow B so as to retract from annulus 67 and thereby expose delivery cavity 76 to gap 34 between abdominal wall 12 and peritoneum 16. Blunt tip 40 and guidewire conduit 27 define a guidewire passageway 68 for accommodating guidewire 18 therethrough. Guidewire passageway 68 desirably communicates through the interior of nose body 62 adjacent to annulus 67. It is further contemplated that guidewire passageway 68 may traverse within nose body 62 to exit through centrally located tip 70. Guidewire passageway 68 allows for protected relative displacement between guidewire 18, cannula wall 48, and any tissue separating devices 26 passing through interior passageway 50 to delivery cavity 76.

Cannula 24 is therefore deliverable over guidewire 18 so as to position cannula window 52 within gap 34 proximal to the herniated region 14. Cannula 24 accommodates tissue dissection devices 26 of the present invention extending from delivery cavity 76 through cannula window 52 for separating the abdominal wall 12 from the peritoneum 16 as will be hereinbelow described. Each tissue dissection device 26 may form operating space 28 in registry with the myopectineal orifice 32.

3. Tissue Dissection Devices

A. Balloon Dissection Devices

The present invention provides alternate embodiments for a tissue dissection device 26 which may be delivered along guidewire 18 to form a bloodless operating cavity. With reference to FIGS. 6–29, a tissue dissection device 26 of the present invention may take the form of a balloon dissection device 60. Each variant of balloon dissection device 60 of the present invention incorporates cannula 24 and further provides an inflatable tissue-separating balloon 74, as generally represented in FIGS. 6 and 7. Tissue-separating balloon 74 is deliverable within delivery cavity 76 in a collapsed configuration and is expandable to an expanded configuration through cannula window 52. Expansion of tissue-separating balloon 74 extends a first wing 74a in a direction diametrically opposite to the direction in which a second wing 74b extends. Wings 74a and 74b extend along a path between the adjacent tissue planes 12 and 16 so as to separate layers 12 and 16 and thereby form operating space 28.

Tissue-separating balloon 74 is desirably formed of a substantially inelastic and surgically suitable material and includes a first major surface 78 peripherally contiguous with an opposing second major surface 80. Balloon 74 further includes a first proximal transverse face 79 and a second distal transverse face 81. The transverse extents of major surfaces 78 and 80 may be joined at a first seam 82a and a second seam 82b, respectively, as shown in FIG. 6, or across a perimetrical face 84, as shown in FIG. 11. Balloon 74 defines a balloon interior 86 in fluid communication with a fluid conduit 72. Fluid conduit 72 extends through passageway 50 in fluid communication between a fluid source, not shown, and balloon interior 86. Both balloon 74 and fluid conduit 72 are formed to provide fluid tight communication with the fluid source.

Balloon 74 may be provided in the collapsed configuration for delivery whereby each wing 74a and 74b is alternatingly folded about major surfaces 78 and 80 in a serpentine fashion as shown in FIG. 9. Alternatively, balloon 74 may be provided in the collapsed configuration for delivery by rolling balloon 74 from distal end 81. The fully rolled balloon may then be compressed to effectively form opposing creases 78' and 80' in surfaces 78 and 80 so as to conform to delivery cavity 76 as shown in FIG. 10.

The operation of the tissue-separating balloon is substantially the same regardless of the form finally selected. The present invention contemplates delivering balloon 74, in a collapsed configuration within delivery cavity 76 of device 60. Once device 60 is properly positioned within gap 34, sheath 64 will be pulled in the direction of arrow B away from nose body 62 to fully expose collapsed balloon 74. The fluid source will supply a fluid, desirably a saline solution, through fluid conduit 72 into balloon interior 86. The internal pressure provided by the fluid will cause balloon 74 to expand outwardly from device 60 to assume an expanded configuration Expansion may further be aided by providing a pulsating excitement to the fluid, as is known in the art. Operating space 28 will be fully realized through either the expansion of, or the final expanded configuration assumed by, balloon 74. Once balloon 74 is fully expanded, the direction of flow from the fluid source may be reversed so as to remove the fluid from balloon interior 86 and thereby deflate balloon 74. Once deflated, balloon 74 may be withdrawn from operating space 28 through either of punctures 36 or 38. The present invention also contemplates disconnecting balloon 74 from fluid conduit 72 so as to leave balloon 74 in place over operating space 28 as will be described in further detail hereinbelow.

Figure 6A:
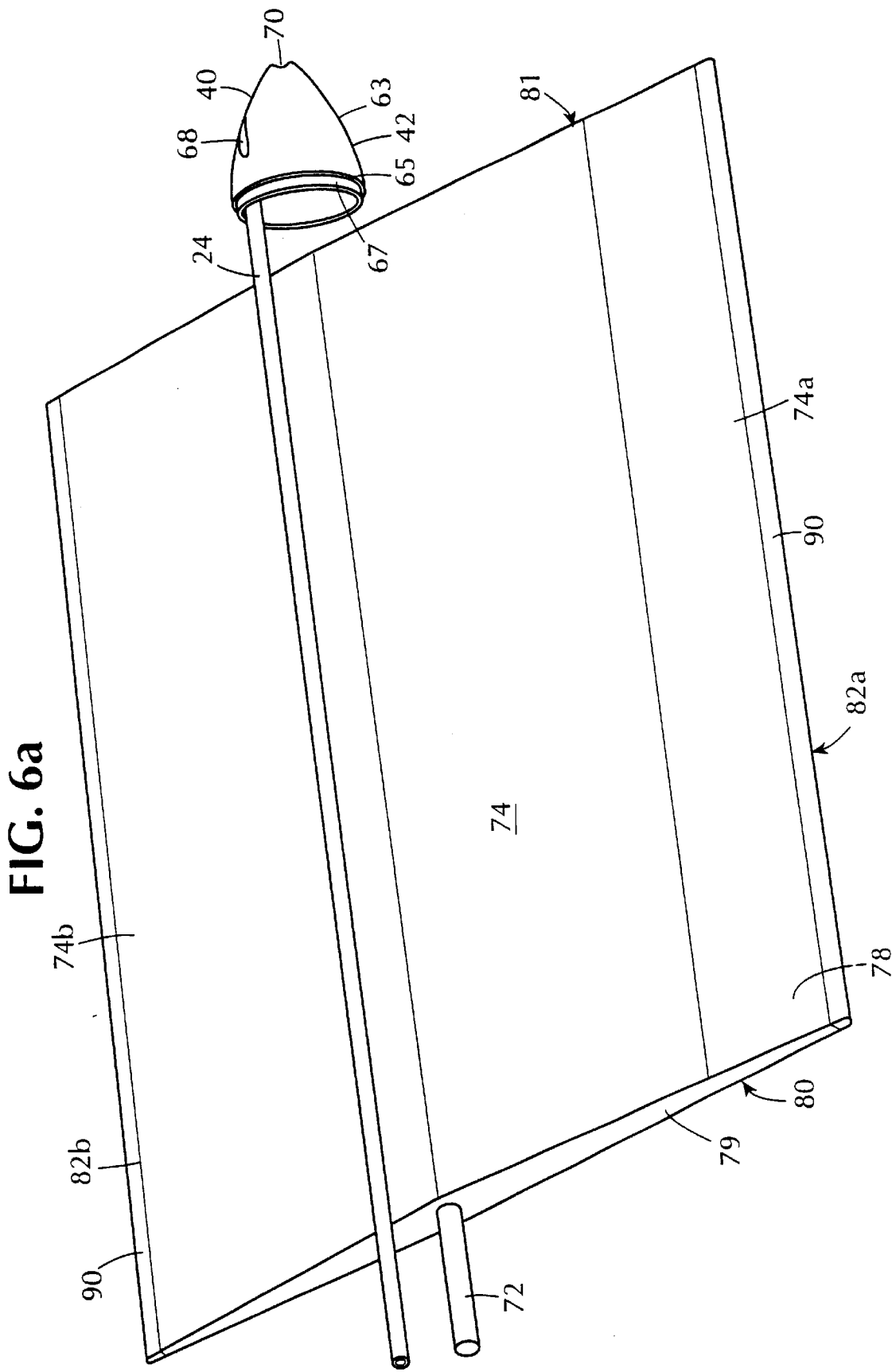
FIG. 6 shows a tissue separating balloon of the present invention.
Figure 8:
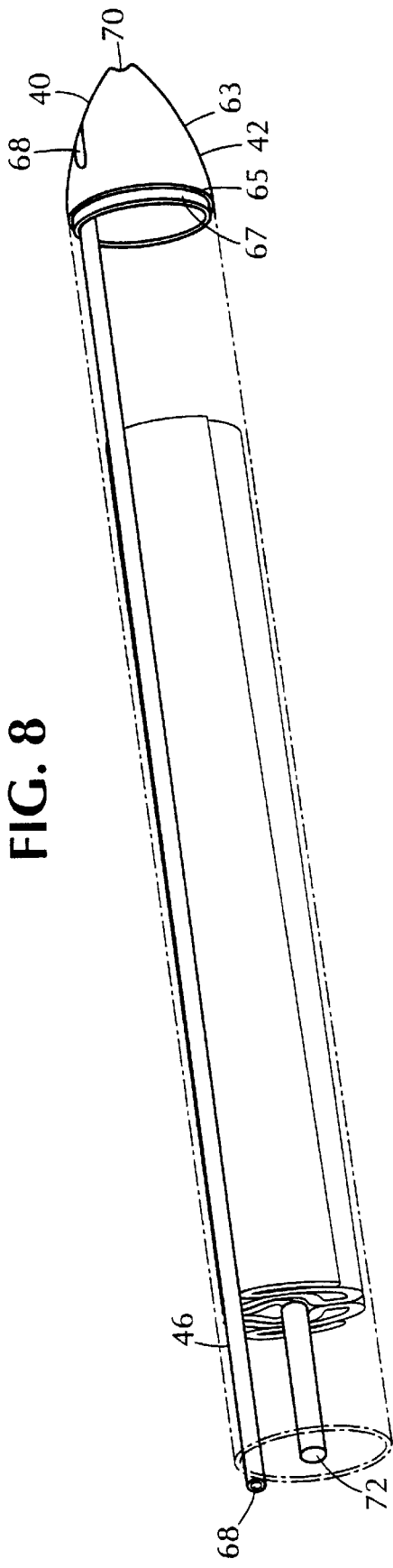
FIG. 8 is a partial cutaway view of the cannula of FIG. 7.

Referring now to FIG. 6a, it is contemplated that tissue dissection may be further aided by further providing balloon 74 with a rigid dissection tip 90 along each of seams 82a and 82b. Dissection tip 90 desirably included a leading edge 92 which is pushed between adjacent tissue layers 12 and 16 as balloon 74 is inflated. Dissection tip 90 may be formed of a suitable surgical plastic material. Dissection tip 90 may alternatively be formed by a metallic material which may be excited by an external stimulus, such radio frequency energy, so as to vibrate and further induce separation of tissue layers 12 and 16. Suitable metallic materials are well known in the art.

Other variants of balloon 74 contemplated by the present invention will now be discussed. Similar numbering of similar components which perform similar functions is employed when possible. Each variant of balloon 74 may be delivered along guidewire 18 to a position within gap 34 so as to be expandable between adjacent tissue layers 12 and 16 and form operating space 28. Each balloon is inflatable by a fluid as described hereinabove. Tissue dissection by each balloon may be further aided by providing a pulsating excitation to the fluid as the balloon is expanded. Additionally, while not shown, the present invention contemplates that each balloon variant may further include a dissection tip 90 as described hereinabove.

Tissue separating balloon 74 may take the form of a diverging frustum balloon 174 as shown in FIGS. 11–16. Balloon 174 is said to be diverging as each of major surface 178, 179, 180, and 181 are seen to be diverging from a smaller central portion 175 which is longitudinally aligned with fluid conduit 172. Balloon 174 includes a pair of opposed distal faces 184a and 184b which perform the majority of the tissue-separating function. Balloon 174 provides a desirable shape for collapsing balloon 174 into a contracted configuration within balloon interior 186 for delivery. As each of surfaces 178, 179, 180, and 181 taper outwardly from the central portion 175 when balloon 174 is in the expanded configuration, balloon 174 may be collapsed within interior 186 so as to minimize its profile in the collapsed configuration. As shown in FIGS. 15 and 16, the collapsed configuration of balloon 174 is achieved by similarly pleating surfaces 178, 179, 180, and 181 so that distal faces 184a and 184b are exposed to gap 34 when sheath 164 is retracted. Interior surface 184a of distal face 181 may therefore be provided in unobstructed fluid communication across from inlet port 177 to thereby ensure reliable balloon expansion.

Distal face 184 is desirably formed having a longitudinal length equal to one dimension of the desired operating space 28 to be formed as distal face 184 extends transversely from central portion 175 during inflation. As balloon 174 expands to its fully inflated configuration, distal face 184 will have pushed open at least a portion of operating space 28 even though balloon 174 will only partially thereoccupy. Alternatively, balloon 174 may provide distal faces 184a and 184b transversely spaced a distance equal to the length of the other major dimension of the desired operating space 28 to be formed so that inflation of balloon 174 will separate a operating space 28 of the desired dimensions.

With reference to FIGS. 17–19, the present invention further contemplates providing a tissue-separating balloon 274 taking the form of a converging frustrum as each of major surfaces 278, 279, 280, and 281 taper from a larger central portion 275 to smaller transversely-extending distal ends. Balloon 274 includes a pair of opposed wings 274a and 274b and a pair of opposed distal edges 282a and 282b which perform the majority of the tissue-separating function. Balloon 274 provides a desirable shape for collapsing balloon 274 into a contracted configuration within balloon interior 286 for delivery as shown in FIGS. 18–19. As each of surfaces 278, 279, 280, and 281 taper outwardly from the central portion 275 when balloon 274 is in the expanded configuration, balloon 274 may be collapsed within interior 286 so as to minimize its profile in the collapsed configuration. As shown in FIGS. 18 and 19, the collapsed configuration of balloon 274 is achieved by similarly pleating surfaces 278, 279, 280, and 281 so that distal edges 282a and 282b are exposed to gap 34 when sheath 264 is retracted. Interior edge 286a of distal edge 282 may therefore be provided in unobstructed fluid communication across from inlet port 277 to thereby ensure reliable balloon expansion.

Distal edge 282 is desirably formed having a longitudinal length equal to one dimension of the desired operating space 28 to be formed as distal edge 282 extends transversely from central portion 275 during inflation. As balloon 274 expands to its fully inflated configuration, distal edges 282a and 282b will have pushed open at least a portion of operating space 28. Alternatively, balloon 274 may further provide distal edges 282a and 282b transversely spaced a distance equal to the length of the other major dimension of the desired operating space 28 to be formed so that inflation of balloon 274 will separate a operating space 28 of the desired dimensions.

Figure 21:
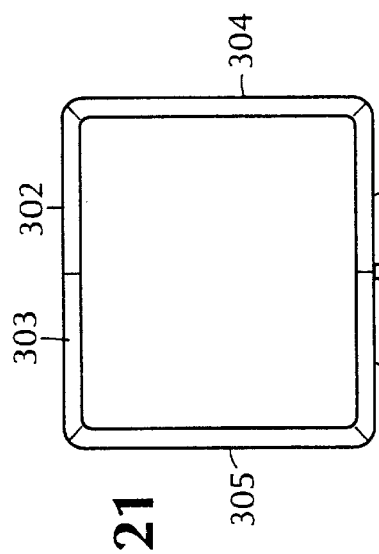
FIGS. 20 and 21 depict still another tissue separating balloon of the present invention.
Figure 20:
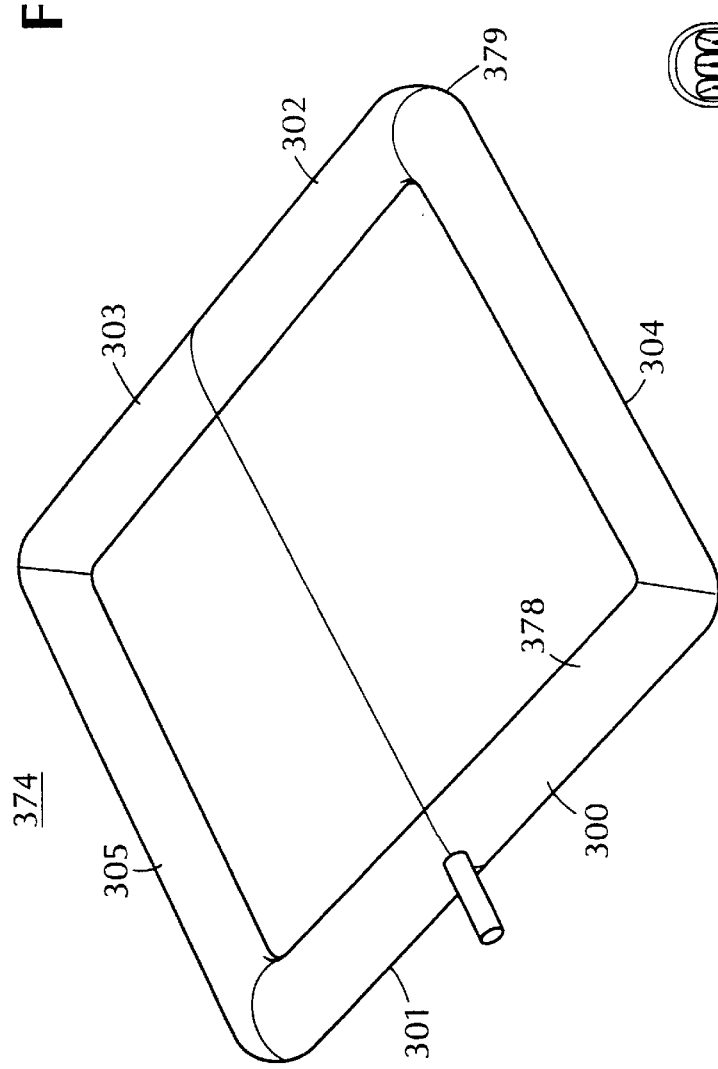
Figure 41:
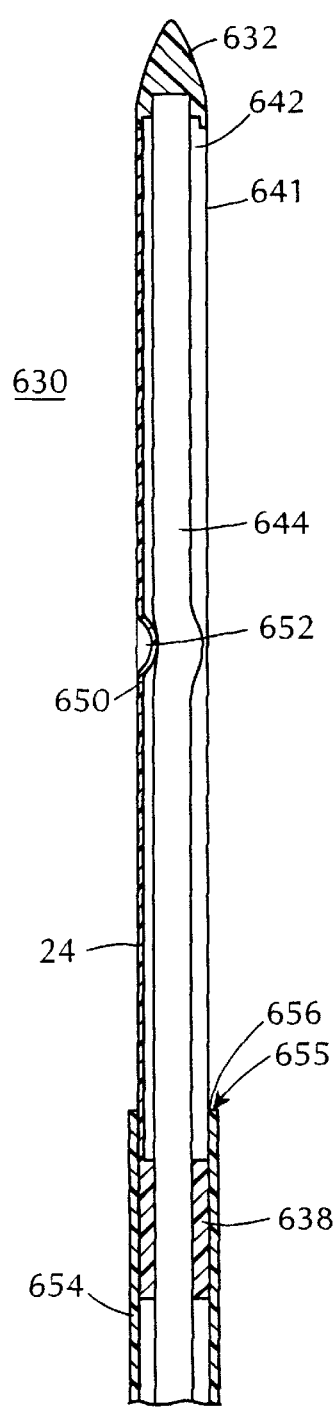

Referring now to FIGS. 20–23, the present invention further contemplates a tissue-separating balloon 374 having an elongate hollow tubular wall having a substantially rectangular frame shape so as to define the outer perimeter of operating space 28 in the expanded position. Tissue-separating balloon 374 is advantageous in that it requires less material than a planar structure such as those shown previously and may therefore require a smaller delivery cavity defined by a smaller diameter delivery device. With reference to FIGS. 20–21, tissue separating balloon 374 is defined in an expanded position by two pair of transverse balloon segments 300, 302 and 301, 303 extending in fluid communication from fluid conduit 372 to opposite ends of a pair of elongate longitudinally-oriented tubular balloon segments 304 and 305, respectively. In the expanded position, tissue-separating balloon 374 desirably defines the perimeter of the operating space 28.

Figure 22:
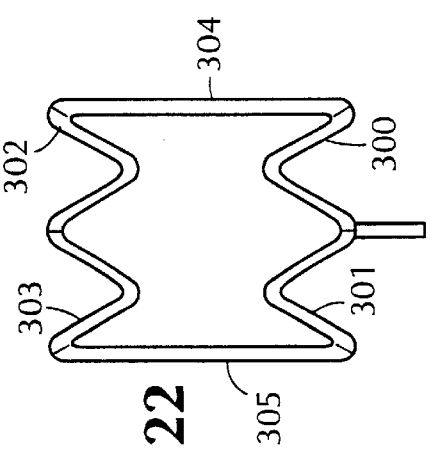
FIG. 22 depicts the folding of the tissue separating balloon of FIGS. 20 and 21 for delivery within a cannula of the present invention.
Figure 23:
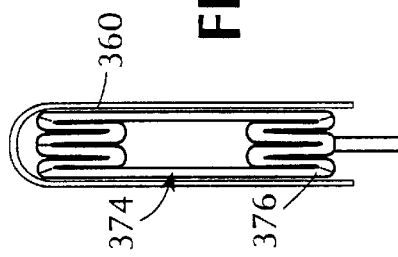
FIG. 23 depicts the tissue separating balloon of FIGS. 20 and 21 within a delivery cannula of the present invention.

Referring now to FIGS. 22–23, balloon 374 may be provided in a collapsed configuration by folding balloon segments 300, 301, 302, and 303 at their respective midpoints 300a, 301a, 302a, and 303a so as to be deliverable within delivery cavity 276 of balloon dissection device 260. While balloon 374 is shown to have a rectangular perimetrical shape, other configurations for balloon 374 may be provided depending on the particular shape of the operating space desired to be created without departing from the teachings of the present invention.

A still further configuration for the balloon of the present invention is depicted in FIGS. 24 and 25, wherein balloon 474 is provided as part of balloon dissection device 460 and as having two asymmetrically extending inflatable balloon wings 474a and 474b. The present invention contemplates delivering balloon dissection device 460 along the diagonal of a rectangular operating space 28 to be positioned in registry with an operating site such as the myopectineal orifice 32. It can be appreciated from FIG. 24 that balloon wings 474a and 474b are similarly formed but longitudinally reversed with respect to dissection device 460. Balloon 474a will therefore be described in detail as also representative of the construction and operation of balloon 474b.

Balloon 474a includes opposed major surfaces 478 and 480 being peripherally contiguous across sidewalls 479 and 481. Surfaces 478 and 480 and sidewalls 479 and 481 define balloon edges 478a, 478b, 480a, and 480b extending from central portion 475 of balloon 474 and converging upon a distal apex 485 opposite central portion 475. Balloon 474a defines a balloon interior 486 in fluid communication with fluid conduit 472. As shown in FIGS. 27, balloon 474a may be provided in the collapsed configuration for delivery whereby balloon 474a is alternatingly folded about major surfaces 478 and 480 in a serpentine fashion. Alternatively, as shown in FIG. 28, balloon 474a may be provided in the collapsed configuration for delivery by rolling balloon 474a from distal apex 485. The fully rolled balloon may then be compressed to effectively form opposing creases 478' and 480' in surfaces 478 and 480 so as to conform to delivery cavity 476.

As shown in FIG. 29, the collapsed configuration of balloon 474a may also be achieved by similarly pleating major surfaces 478 and 480 so that distal apex 485 faces gap 34 when sheath 464 is retracted for delivery. Interior apex 485a of distal apex 485 may therefore be provided in unobstructed fluid communication across from inlet port 477 to thereby ensure reliable balloon expansion. Like balloon 274, balloon 474a may be delivered in this pleated manner so as to minimize its profile in the collapsed configuration. It is desirable for balloon 474a to be sized to form about one half of operating space 28 so that the longitudinally reversed balloons 474a and 474b together provide the desired operating space 28 in registry with the operating site.

B. Mechanical Blade Dissection Devices

The present invention also contemplates that tissue dissection device 26 may take the form of a mechanical device which may be delivered to gap 34 along guidewire 18 and operate to form a bloodless operating cavity. Referring now to FIGS. 30–38, the present invention provides a transversely extendable and retractable elongate tissue dissection device 600. Device 600 incorporates cannula 24 and further provides an elongate tissue dissection blade 602 having an arcuate surface 604 coextensive with a portion of cannula window 52. Device 600 desirably is deliverable along guidewire 18 into gap 34 at which point sheath 64 may be retracted from a position enclosing blade 602 to a position whereby blade 602 may be extended into gap 34 between adjacent tissue layers 12 and 16 so as to form operating space 28 in registry with the myopectineal orifice 32 of a patient. Surface 604 is desirably a blunt arcuate surface so as to minimize the risk of blade 602 burrowing through a tissue layer as it is extended from device 600.

With reference to FIGS. 31–33, blade 602 includes a first end 606, a second end 608 and an elongate oblong blade body 610 extending therebetween. Oblong blade body 610 includes arcuate surface 604 along one major surface thereof and an opposing arcuate major surface 612. Blade 602 supports a pair of orthogonally-oriented elongate pusher rods 614 and 616 adjacent ends 606 and 608 respectively. Pusher rods 614 and 616 extend from fixed ends 614a and 616a to free ends 614b and 616b respectively. Blade 602, including pusher rods 614 and 616, is desirably formed of a suitable flexible plastic material such as polypropylene.

As shown in FIG. 32, pusher rods 614 and 616 have substantially rectangular cross-sections defined between a pair of major surfaces 618a, 618b and 620a, 620b, all of which are acutely oriented with respect to the longitudinal axis of blade 602. As shown in FIG. 30, each of pusher rods 614 and 616 are acutely oriented so as to be receivable in a pair of elongate passageways 622 and 624 formed within delivery cavity 76. Each passageway 622 and 624 extends from a first end 622a and 624a defined at access aperture 44 to a second end 622b and 624b opening in fluid communication with cannula window 52, respectively. Passageways 622 and 624 have dimension closely conforming to the cross-sectional dimensions of pusher rods 614 and 616 so as to minimize buckling deflection of the pusher rods about major surfaces while therein.

With additional reference to FIGS. 34 and 37, each of passageways 622 and 624 are further shaped so as to orthogonally turn and longitudinally twist pusher rods 614 and 616, respectively, towards parallel alignment as each extends from access aperture 44. As blade 602 is positioned within cannula window 52 for delivery, free end 614b and 616b extend out from access aperture 44 for grasping by a surgeon. As shown in FIG. 37, longitudinal movement of free ends 618 and 620 in the directions of arrows C and D causes the transverse movement of blade 602 in the directions of arrows E and F, respectively. The acute alignment of pusher rods 614 and 616 at fixed ends 614a and 616a ensures that major surfaces 618a, 618b, and 620a, 620b are turned towards each of the adjacent tissue layers 12 and 16. With this orientation, tissue layers 12 and 16 may help pusher rods 614 and 616 resist buckling during extension from cannula window 52. Should the buckling of one pusher rod become too severe, the surgeon can simply retract both pusher rods in the direction of arrow D until the slack in the buckling pusher rod is taken up. The surgeon may then apply light pressure with one hand on the patient's abdomen to further help restrain longitudinal buckling of the pusher rod.

Device 600 is desirably provided along a centerline bisecting the myopectineal orifice. Extension of blade 602 from the centerline may therefore open approximately one half of operating space 28 at which point blade 602 would be retracted back within cannula window 52. The surgeon would then rotate device 180 degrees about its longitudinal axis so that blade 602 faces in an opposite transverse direction so as be positioned to separate tissue layers 12 and 16 and fully form operating space 28. Once the operating space is fully formed, blade 602 is retracted back within cannula window 52 and device 600 may be removed therefrom.

Referring now to FIGS. 39–43, the present invention provides an extendable tissue-separating device 630 deliverable along guidewire 18. Tissue-separating device 630 conforms to the general design of cannula 24 by providing a blunt nose 632 at one end of an elongate cannula wall 634 having a guidewire conduit 636 extending therealong and through blunt nose 632. Tissue separating device 630 includes a proximal housing 638 accommodating guidewire conduit 636 and a dissection member passageway 640. Cannula wall 634 defines both a cannula interior 641 and an elongate window 642 extending from housing 638 towards blunt nose 632. During use, proximal housing 638 desirably extends from gap 34 through the abdominal wall 12 and is exposed to, and accessible by, a surgeon. Tissue-separating device 630 accommodates retractable sheath 64, shown in phantom lines, so as to provide easier insertion thereof into gap 34. Sheath 64 may be retracted from blunt nose 632 over housing 638 so as to expose an elongate tissue-separating member 644. Tissue-separating device 630 may be formed having a very small diameter in that it need only accommodate guidewire 18 and a similarly-sized tissue-separating member 644. While it is contemplated that tissue separating device 630 has an external diameter of about 10 millimeters, it is also contemplated that the diameter may be about 5 millimeters and preferably about 2 millimeters.

Tissue-separating member 644 extends from an anchored end 644a at blunt nose 632 through dissection member passageway 640 of housing 638 to a free end 644b and includes a body portion 644c extending therebetween. Anchored end 644a may be conventionally fixed within a receiving cavity 646 defined by a base surface 648 of blunt nose 632 or otherwise positioned there adjacent so as to be flexible thereabout. Body portion 644c is extendable and retractable through window 642 by actuation of free end 644b in the direction of arrows G and H, respectively. Tissue-separating member is desirably formed of a flexible yet resilient material such as stainless steel or a suitable surgical plastic such that body portion 644c buckles and extends through cannula window 642. As free end 644b is moved further in the direction of arrow G, body portion 644c will buckle further and extend in the direction of arrow I so as to pass between and separate the adjacent tissue layers 12 and 16 and thereby define operating space 28 of the desired dimensions.

It is contemplated that tissue separation using device 630 may require a reciprocating motion of free end 644a in the directions of arrows G and H so as to deflect body portion 644c in the directions of arrows I and J such that with ever increasing stroke lengths in the direction of arrow G will cause a larger deflection in the direction of arrow I so as to thereby increase the size of the opened operating space 28. It is further contemplated that an external excitation force such as a radio frequency vibration may be applied to tissue-separating member 644 to further assist in separating adjacent tissue layers 12 and 16. As with device 600, a surgeon may apply light pressure with one hand on the patient's abdomen to help maintain the buckling of tissue-separating member 644 within the plane between the adjacent tissue layers 12 and 16.

The dimensions of the operating space 28 provided by tissue separating device 630 is chiefly a function of the longitudinal length of cannula window 642 and the length of tissue-separating member 644 fed through proximal housing 638 by a surgeon. The present invention contemplates that the length of cannula window 642 may be fixed for a given device 630. Furthermore, the present invention contemplates that the length of cannula window 642 may be made selectable by providing an elongate rigid hollow duct 654 including a first end 655 defining an opening 656. Duct 654 is formed to slide over the outside of proximal housing 638 and cannula 24 so as to position first end 655 over a portion of cannula window 642 to thereby reduce the opening through which tissue-separating member 644 may extend. It is also contemplated that duct 654 may be formed so as to pass through the interior of proximal housing 638 and about tissue separating member 644. Duct 654 thereby allows an operator to select the size of cannula window 642 and thereby precisely control the size of operating space 28 created by the extension of tissue-separating member 644.

While tissue-separating member 644 is shown as depicted in FIG. 40a as an elongate wire having a circular cross-section, it is contemplated by the present invention that the actual cross section of tissue-separating member 644 may be formed so as to favor buckling in the direction of arrow I when free end 644b is moved in the direction of arrow G towards blunt nose 632. FIGS. 40b–d show alternative cross-sections of tissue dissecting member 644 which may enhance buckling in the desired manner. Figure B depicts a crescent shape cross section in which an outer surface 644d faces towards cannula window 642. FIG. 40 depicts an oval cross sectional shape having a first cross sectional axis 644e and a second longer cross sectional axis 644f. The guidewire of FIG. 40c positions an outer surface 644d facing towards cannula window 642 and buckles about the longer cross sectional axis 644f. FIGS. 40d–e show a tissue-separating member 644 having a helical thread 644g formed therealong which assists in the separation of adjacent tissue layers 12 and 16. It is also contemplated by the present invention that device 630 may provide an elongate interior wall 650 extending within cannula interior 641 adjacent to tissue-separating member 644 so as to prevent buckling in an unintended direction. Interior wall 650 desirably further provides a bowed surface 652 extending against tissue-separating member 644 to further predispose buckling in a desired manner.

It is further contemplated that tissue-separating device 630 may create an operating space 28 extending to opposite sides of guidewire 18. After having opened a portion of operating space 28 to one side of guidewire 18, tissue-separating member 644 may be retracted through cannula window 642 and tissue-separating device 630 may then be rotated 180 degrees about its longitudinal axis 1. Once so rotated, tissue-separating member 644 may again be extended through cannula window 642 as before to thereby enlarge operating space 28.

Figure 44:
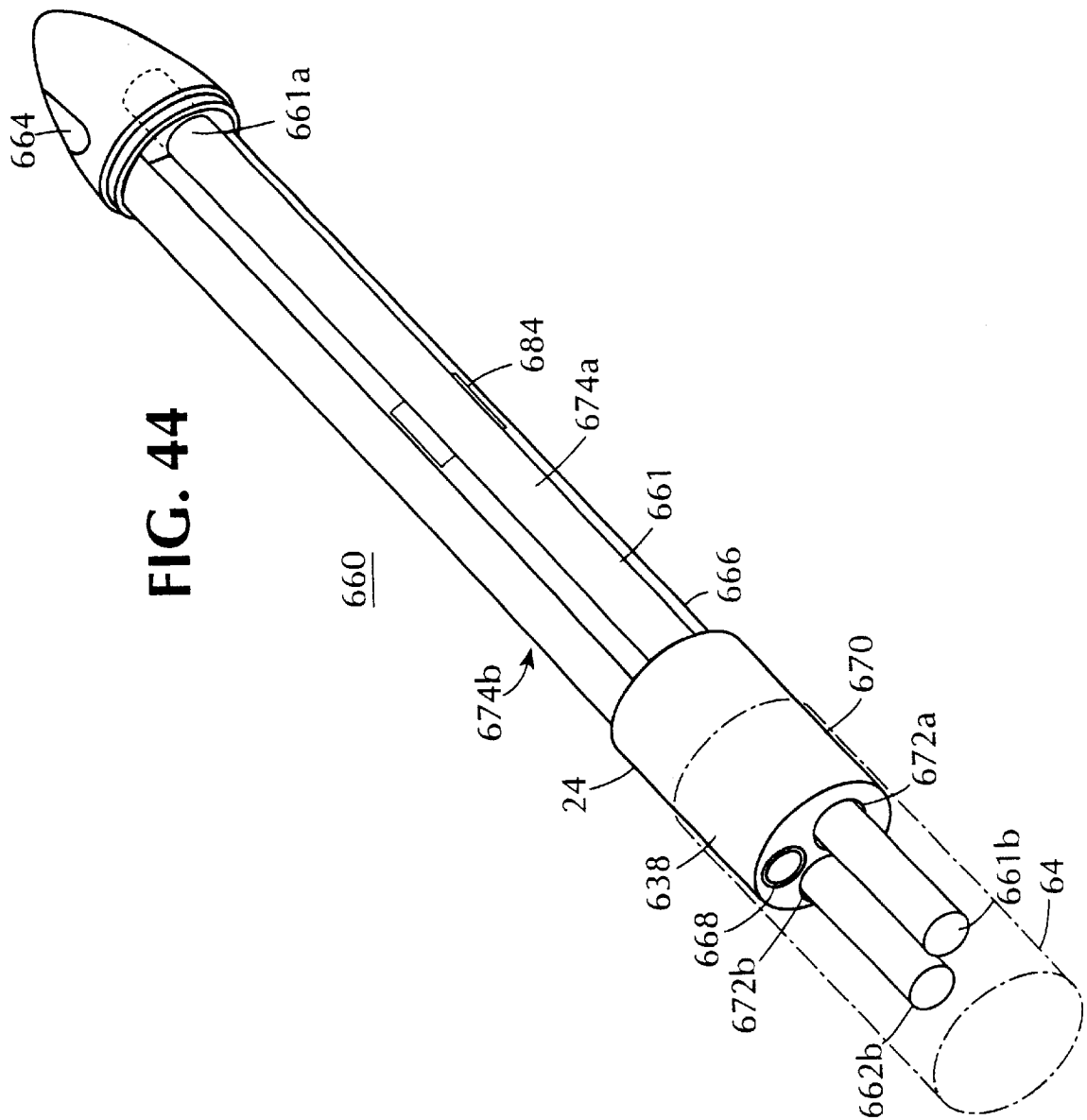
FIGS. 44 and 45 depict an alternate embodiment of the tissue separating device of FIGS. 39–43 employing two tissue separating members.
Figure 45:
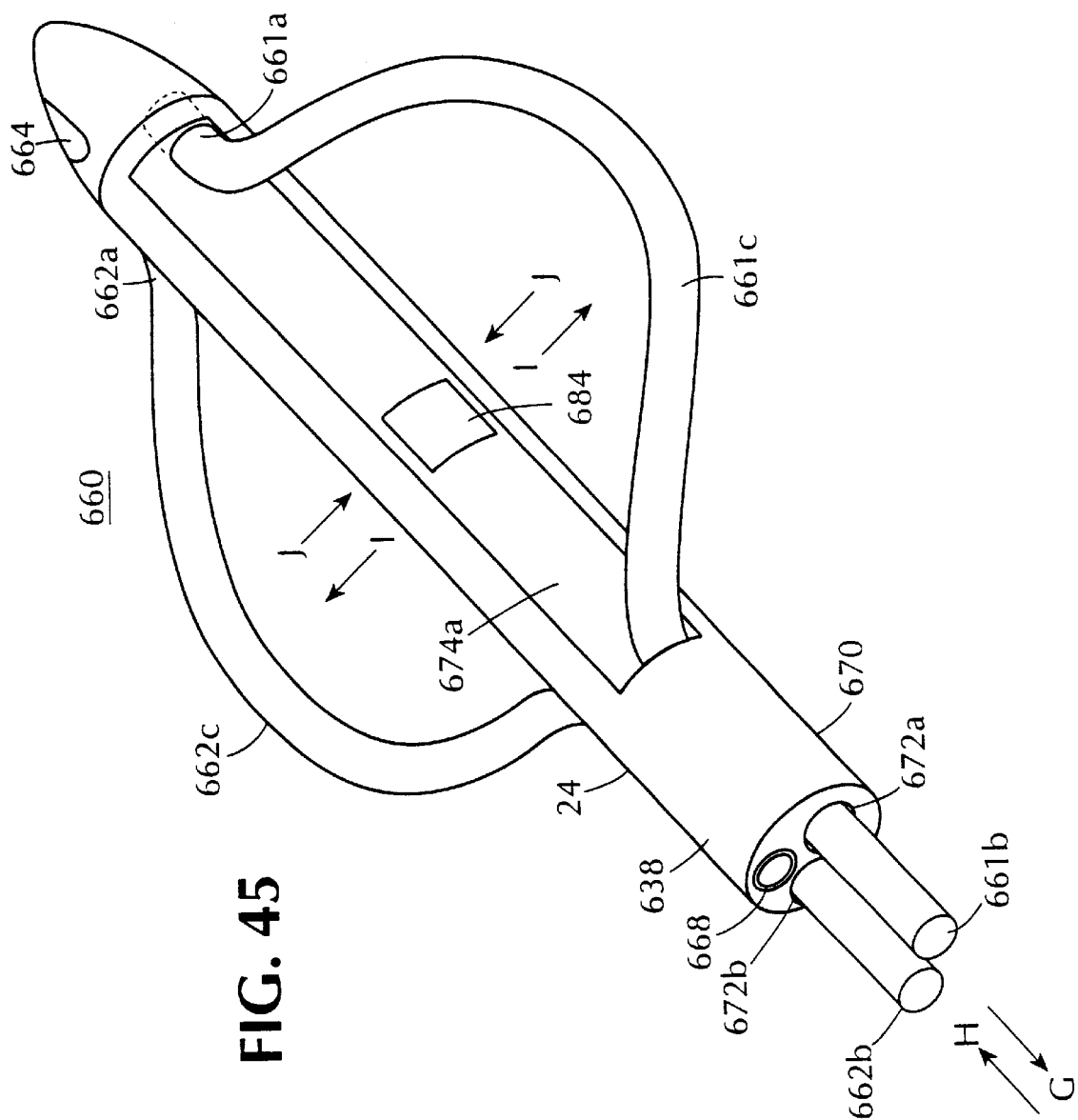

Alternatively, as shown in FIGS. 44–45, the present invention contemplates a dual-extending tissue-separating device 660 having a first elongate tissue separating member 661 which may be extended simultaneously with, and oppositely to, second tissue separating member 662. Tissue-separating device 660 incorporates many of the same features as tissue-separating device 630 and conforms to the general design of cannula 24 by providing a blunt nose 664 at one end of an elongate cannula wall 666 having a guidewire conduit 668 extending therealong and through blunt nose 664. Tissue separating device 660 includes a proximal housing 670 accommodating guidewire conduit 668 and first and second dissection member passageways 672a and 672b. Cannula wall 666 defines both a cannula interior 673 and a first and second oppositely-disposed elongate windows 674a and 674b extending from housing 670 towards blunt nose 664. During use, proximal housing 670 desirably extends from gap 34 through the abdominal wall 12 and is exposed to, and accessible by, a surgeon. Tissue-separating device 660 accommodates retractable sheath 64, shown in phantom lines, so as to provide easier insertion thereof into gap 34. Sheath 64 may be retracted from blunt nose 664 and over housing 670 so as to expose tissue-separating members 661 and 662. Tissue-separating device 660 may be formed having a very small diameter in that it need only accommodate guidewire 18 and a similarly-sized tissue-separating members 661 and 662. While it is contemplated that tissue separating device 660 has an external diameter of about 10 millimeters, it is also contemplated that the diameter may be about 5 millimeters and preferably about 2 millimeters.

Tissue-separating members 661 and 662 extend from anchored ends 661a and 662a at blunt nose 664 through respective dissection member passageways 672a and 672b of housing 670 to free ends 661b and 662b and include body portions 661c and 662c extending therebetween, respectively. Anchored ends 661a and 662a may be conventionally fixed within receiving cavities 646a and 646b defined by base surface 680 of blunt nose 664 or otherwise positioned thereadjacent so as to be flexible thereabout. Body portions 661c and 662c are extendable and retractable through windows 674a and 674b, respectively, by actuation of free end 661b and 662b in the direction of arrows G and H. Tissue-separating members 661 and 662 are desirably formed of a flexible yet resilient material such as stainless steel or a suitable surgical plastic such that body portions 661c and 662c buckle and extend through cannula windows 674a and 674b. As free ends 661b and 662b are moved further in the direction of arrow G, body portions 661c and 662c buckle further and extend in the direction of arrow I away from cannula wall 666 so as to pass between and separate the adjacent tissue layers 12 and 16 and thereby define operating space 28 of the desired dimensions.

It is contemplated that tissue separation using device 660 may require a reciprocating motion of free end 661a and 662a in the directions of arrows G and H so as to deflect body portions 661c and 662c in the directions of arrows I and J such that with ever increasing stroke lengths in the direction of arrow G will cause a larger deflections of tissue separating members 661 and 662 to thereby increase the size of the opened operating space 28. It is further contemplated that an external excitation force such as a radio frequency vibration may be applied to tissue-separating members 661 and 662 to further assist in separating adjacent tissue layers 12 and 16. As with device 600, a surgeon may apply light pressure with one hand on the patient's abdomen to help maintain the buckling of tissue-separating members 661 and 662 within the plane between the adjacent tissue layers 12 and 16.

The present invention also contemplates providing a tissue-separating device formed from a shape memory alloy, such as nitinol, through a small diameter cannula Referring now to FIGS. 46–49, the present invention provides a tissue dissection device 700 incorporating cannula 24 and delivering a tissue dissecting bar 702 within delivery cavity 76. Tissue dissecting bar 702 desirably includes a blunt tip 704 at a free end 706 thereof, a shape memory elbow 708 deliverable in a linear configuration as shown in FIG. 46, and an elongate blade body 710 extending therebetween. Bar 702 also includes an elongate pusher rod 712 oppositely positioned across elbow 708 from blade body 710 and extending out access aperture 44 of cannula 24.

Bar 702 is deliverable in a fully martensitic state defined by the linear configuration shown in FIG. 46. Bar 702 is formed of a shape memory alloy composition having an austenitic start temperature slightly below that of body temperature. After bar 702 is delivered within gap 34, body heat will activate bar 702 to assume an austenitic configuration in which elbow 708 deflects to position tip 704 and blade body 710 exteriorly of cannula window 52. Elbow 708 desirably assumes a right-angle configuration so as to extend blade body 710 substantially orthogonal to pusher rod 712, as shown in FIG. 47. Extension of blade body 710 to the right-angle austenitic configuration will simultaneously separate a portion of adjacent tissue layers 12 and 16. Once blade body 710 is fully extended, the surgeon may form operating space 28 by pushing and pulling on pusher rod 712 in the directions of arrows L and M.

After operating space 28 has been formed, blade body 710 may be retracted through window 52 by continued pulling on pusher rod 712 in a withdrawal direction shown by arrow L. While blade 702 is sufficiently rigid to withstand distortion while separating adjacent tissue layers 12 and 16, withdrawal forces blade 702 to deflect against cannula wall 48 to a sufficiently linear alignment for withdrawal of device 700 from operating space 28.

Figure 42:
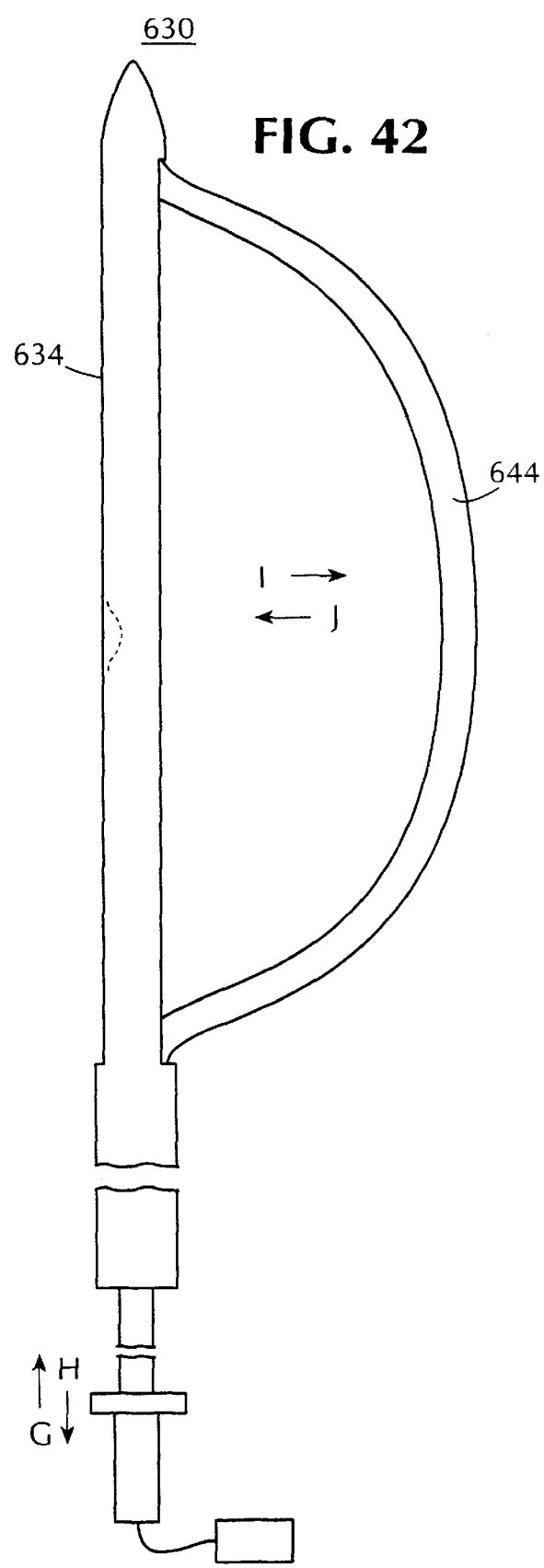
Figure 43:
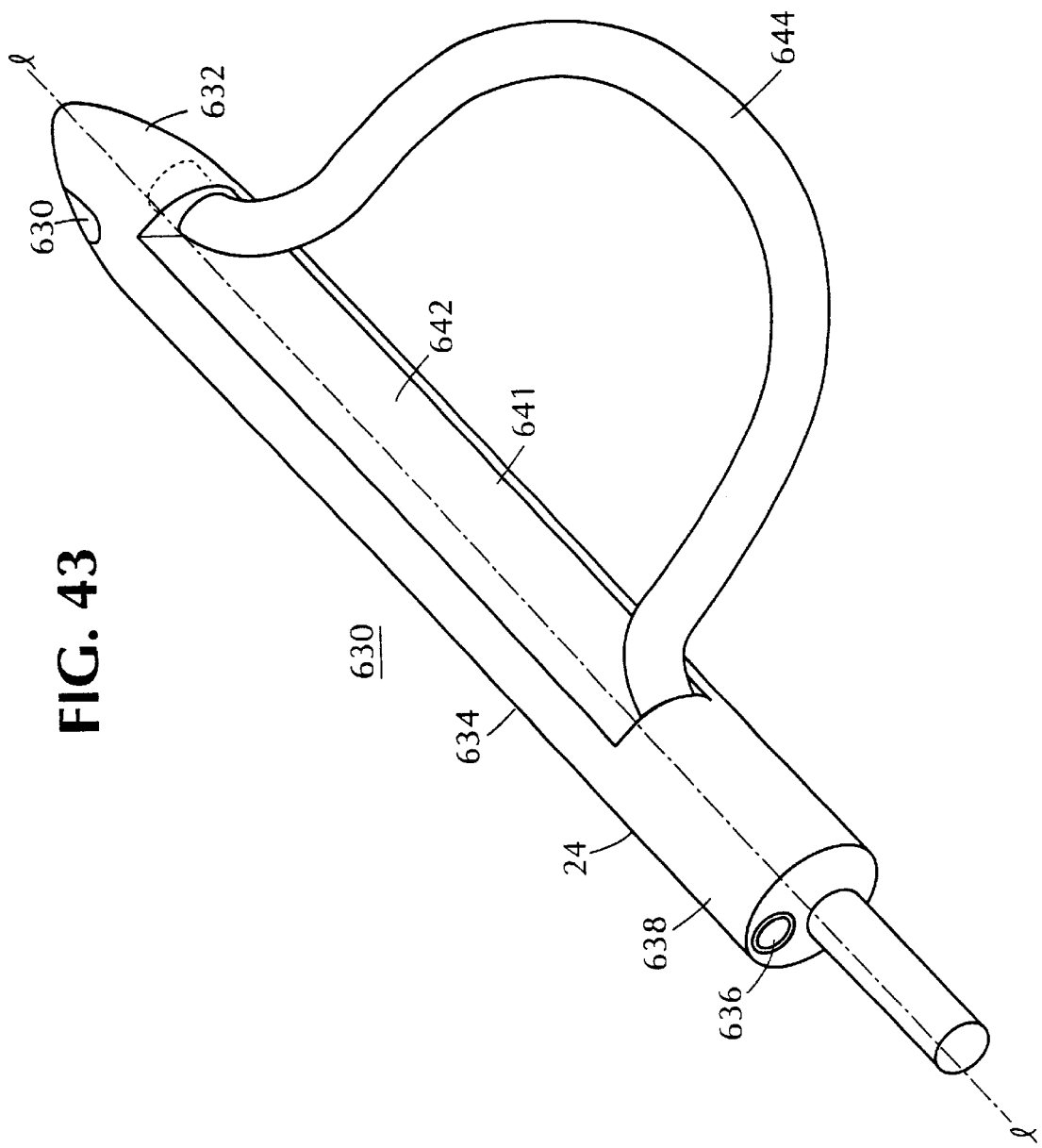
Figure 48:
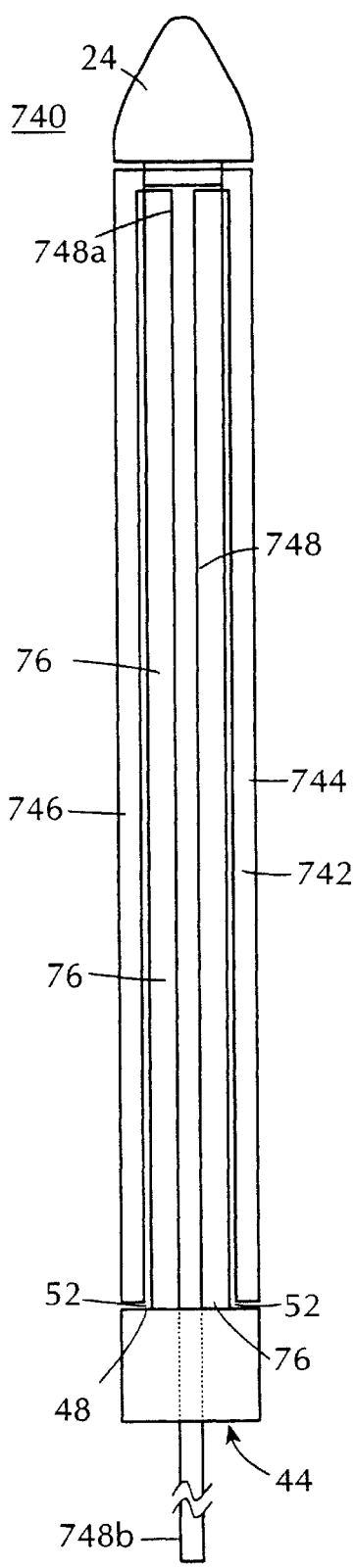
FIGS. 48 and 49 depict an embodiment of the tissue separating device of FIGS. 46 and 47 providing two tissue separating blades formed from a shape memory material.
Figure 49:
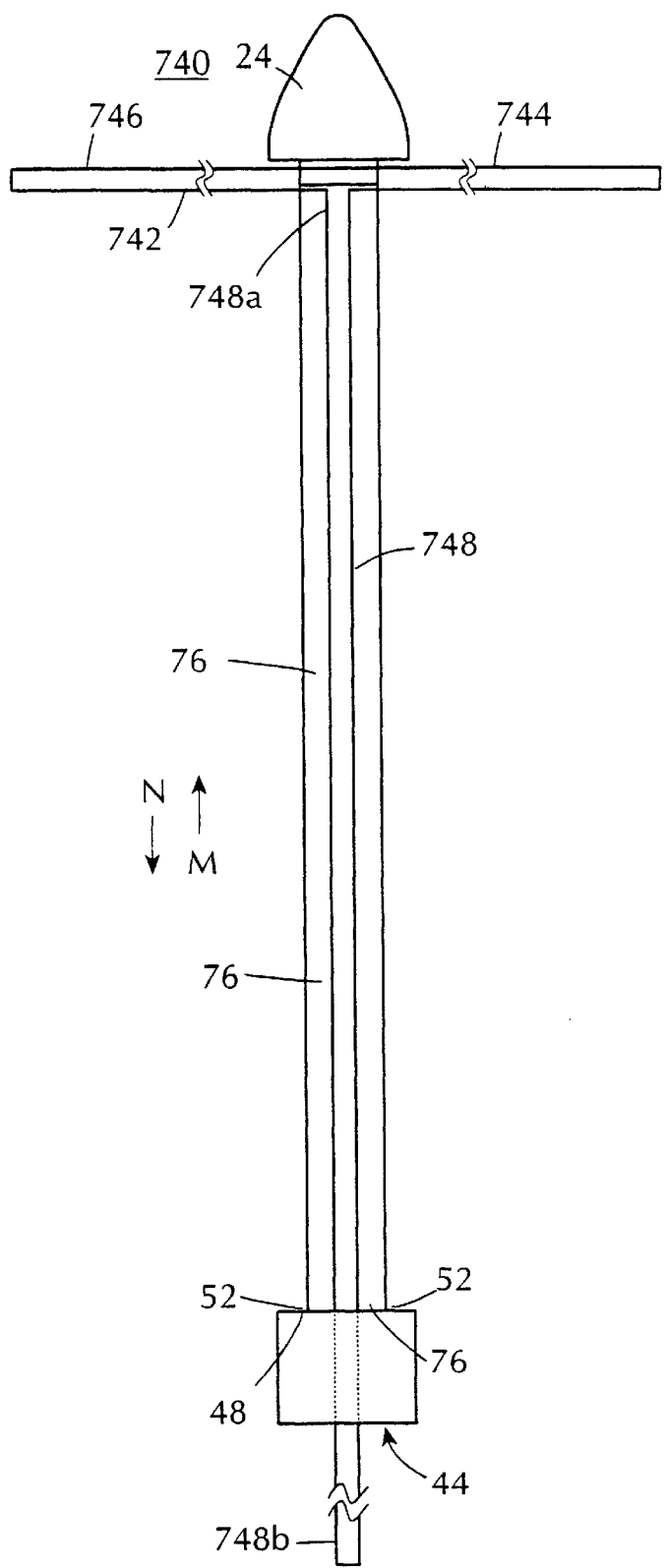

FIGS. 48–49 show an alternate embodiment 740 of tissue-separating device 700. Device 740 incorporates cannula 24 and delivers a tissue-separating blade 742 for separating adjacent tissue layers 12 and 16. Blade 742 is formed of a suitable shape memory alloy and is deliverable in a martensitic state within delivery cavity 72 and is expandable in an austenitic state to extend to radially opposite directions between adjacent tissue layers 12 and 16. Blade 742 includes a first elongate separating member 744 and a second elongate separating member 746 extending from the distal end 748a of a pusher rod 748. In the martensitic state, separating members 744 and 746 are deflected about distal end 748a into parallel alignment with pusher rod 748. Blade 742 is desirably formed having an austenitic start temperature slightly below body temperature so as to expand as shown in FIG. 42 after delivery within gap 34. As further seen in FIG. 49, once separating members 744 and 746 are fully extended, a surgeon may push and pull on a free end 748b of pusher rod 748 in the direction of arrows M and N so as to separate adjacent tissue layers 12 and 16 and thereby define operating space 28. Once operating space is fully formed, blade 742 may be withdrawn back into delivery cavity 76 by pulling pusher rod 748 in a withdrawal direction shown by arrow N. Separating members 744 and 746 are then forced to deflect about distal end 748a by cannula wall 48 until fully within delivery cavity 76, at which time device 740 may be withdrawn from operating space 28.

FIGS. 50–54 illustrate yet another tissue separating device 760 of the present invention. Tissue separating device 760 incorporates cannula 24 and delivers first and second tissue separating blades 762 and 764 for separating adjacent tissue layers 12 and 16. Blade 762 and 764 are formed of a rigid material such as metal or a suitably rigid surgical plastic. Blade 762 and 764 are elongate members having a proximal end 762a and 764a and a distal end 762b and 764b, respectively. Blade 762 and 764 pivot about proximal end 762a and 764a from a stored configuration enclosed within cannula 24 to an extended configuration projecting between adjacent tissue layers 12 and 16. As shown in FIG. 51, blade 762 and 764 pivot about a pivot pin 766 affixed to a pivot base 768 of a blade support 770. Blade support 770 further provides a transversely oriented blade stop 772 including a blade stop surface 773 adjacent pivot pin 766. Blade stop surface 773 prevents over rotation of blades 762 and 764 when extended between adjacent tissue layers 12 and 16.

Tissue separating device 760 further includes an elongate hollow guide sleeve 786 affixed about blade support 770 so as to provide a bushing for the sliding extension and retraction of an elongate actuating rod 774 therethrough. The distal end 770a of actuating rod 774 includes a transversely-extending deployment wedge 776 having a planar face 777 in facing opposition to blade stop surface 773. Actuating rod 774 and blade support 770 extend through the interior space 779 of a rigid outer sleeve 780 having a rim 782. Tissue separating device 760 defines an operating window 784 between rim 782 of sleeve 780 and blunt nose 40 of cannula 24. Operating window 784 communicates with delivery cavity 76. Rim 782 and operating window 784 are both desirably unveiled as sheath 64 is withdrawn in the direction of arrow A away from blunt tip 40. Blade stop 772 is positionable within cavity 785 so that blades 762 and 764 may be extended and retracted through operating window 784, as will be discussed hereinbelow.

After delivering device 760 into gap 34 between tissue layers 12 and 16, the operator retracts sheath 64 away from blunt nose 40 in the direction of arrow O to expose operating window 784. In its delivered configuration, actuating rod 774 is positioned in an extended configuration whereby deployment wedge 776 is positioned between distal ends 762b and 764b of blades 762 and 764, as shown in FIG. 50.

The operator then retracts member 774 in the direction of arrow A so as to pull deployment wedge 776 in sliding engagement with the converging blades 762 and 764, causing blades 762 and 764 to pivot away from each other about pivot pin 766. Continued retraction of deployment wedge 776 in the direction of arrow O forces the deployment of blades 762 and 764 through operating window 784 to a deployed configuration as shown in FIG. 53. Deployment of blades 762 and 764 separates adjacent tissue layers 12 and 16 so as to form operating cavity 28 adjacent window 784. Retraction of members 774 and 776 is complete when planar face 777 of member 776 pins proximal end 762a and 764a of blade 762 and 764 against blade support surface 773 so that blades 762 and 764 extend transversely from device 760. Blades 762 and 764 may be held in this extended configuration by maintaining their compression between surfaces 777 and 773.

The operator may then continue to form operating cavity 28 by extending blade support 770 and member 774 in the direction of arrow P towards blunt nose 40. Blades 762 and 764 and operating window 784 are desirably selected with sufficient dimensions that their deployment through operating window 784 and subsequent advancement along the longitudinal expanse of operating window 784 will form an operating cavity 28 of the desired dimensions. It is also contemplated by the present invention that device 760 itself may be moved along the guidewire 17 in the directions of arrows O and P with blades 762 and 764 deployed so as to form an operating cavity 28 having a longitudinal extent greater than that provided by operating window 784.

Referring now to FIG. 54, after the creation of operating space 28, blade 762 and 764 may retracted through window 784 in the following manner. An operator positions blade stop 772 adjacent rim 782 of tube 780. The operator then extends actuating rod 774 in the direction of arrow P until deployment wedge 776 is positioned adjacent blunt nose 40. While maintaining the relative displacement of deployment wedge 776 from blade stop 772, the operator retracts both blade support 770 and actuating rod 774 in the direction of arrow O. Continued retraction in the direction of arrow O forces both blades 762 and 764 against tube rim 782 and their subsequent counter-rotation about pivot pin 766 and towards deployment wedge 774. Once blade 762 and 764 have been retracted through operating window 784 the operator may withdraw device 760 out of the patient through insertion puncture 36.

4. Mesh and Delivery

Each of the tissue dissection devices and methods of the present invention may provide the necessary operating space 28 in which a porous surgical prosthetic mesh 30 may be emplaced to cover an operating site such as a herniated region 14. With reference to FIGS. 55–65, the present invention contemplates that the prosthetic mesh 30 may be either delivered by a balloon dissection device 60 of the present invention simultaneously with the formation of operating space 28, delivered by a second balloon device, or delivered by an alternate means which takes advantage of the operating space 28 previously created by a tissue-dissection device.

Prosthetic mesh 30 is desirably a thin porous surgical mesh which may be emplaced over the herniated region 14. The pores 900 of the prosthetic mesh 30 permit tissue ingrowth therethrough, enabling the mesh to be assimilated by the body so as to form a new tissue layer over the rupture in the herniated region 14. Prosthetic mesh 30 further provides a perimetrical edge 902 defining a boundary providing sufficient overlap of the herniated region. While the art has seen many examples of prosthetic meshes suitable for surgical implantation, one particularly useful thin prosthetic mesh is disclosed by U.S. patent application Ser. No. 08/905,529 presently assigned to Meadox Medicals, Inc., a subsidiary of the present assignee.

A. Mesh Separable from Balloon

Prosthetic mesh 30 may be delivered to operating space 28 either simultaneously with the creation thereof by the expansion of a tissue-separating balloon of the present invention or by inflation of a subsequent mesh-delivery balloon 874 after the creation of operating space 28. While reference is made to a mesh-delivery balloon 874, the present invention contemplates that each of the tissue-separating balloons of the present invention may be utilized for delivery of prosthetic mesh 30 as will be described hereinbelow. For the sake of simplicity, only balloon 814 will be called out in the following description.

Figure 55:
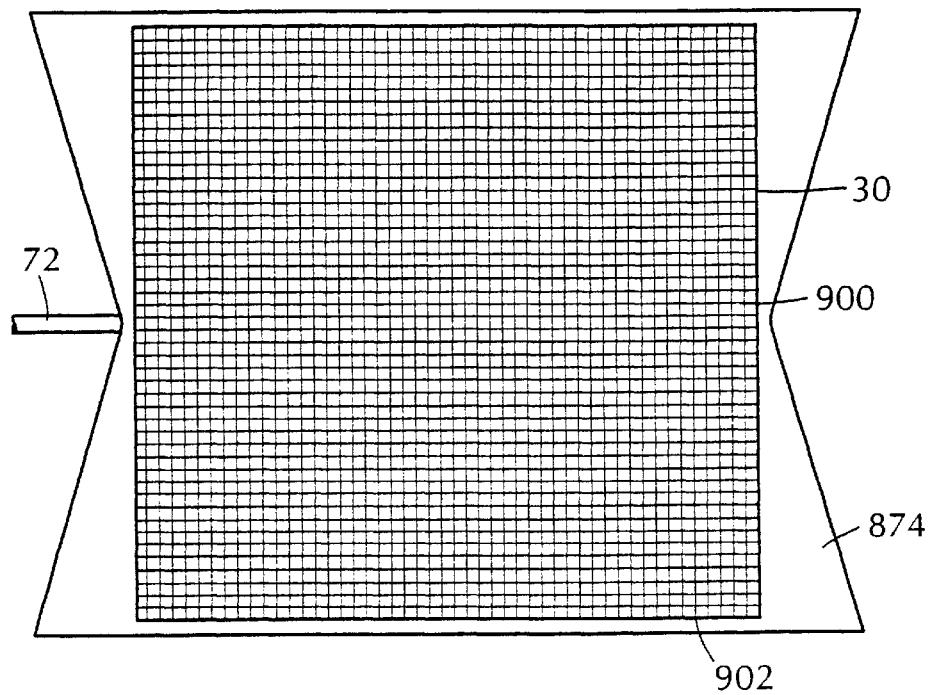
FIG. 55 depicts a tissue separating balloon of the present invention having a detachable prosthesis attached to one major surface thereof.
Figure 56:
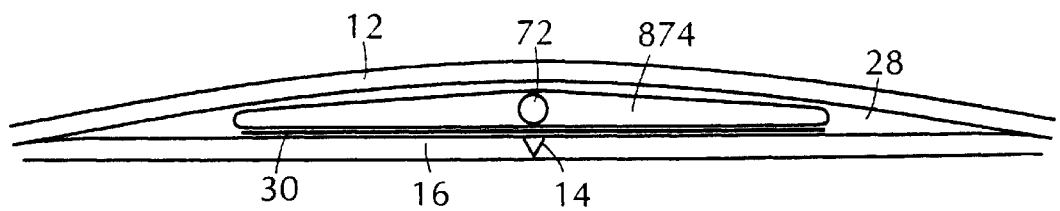
FIG. 56 depicts the tissue separating balloon of FIG. 55 deploying a prosthesis within an operating space created thereby.

Referring to FIGS. 55 and 56, prosthetic mesh 30 is desirably detachably attached across one major surface of a balloon 874 of the present invention and deliverable with balloon 874 by a hollow cannula 24 of the present invention. As balloon 874 is inflated, prosthetic mesh 30 expands from its delivered configuration to a substantially planar configuration to be attached to the abdominal wall 12 by such conventional means as suturing or stapling ox the like and then detached from balloon 874 so as to remain in place over the herniated region 14. Balloon 874 may then be drained of the inflating fluid so as to enable easier extraction through one of the puncture holes 36 or 38. Draining of die inflating fluid may be accomplished by a combination of suction of the fluid through fluid conduit 72 and puncturing of balloon 874 so as to enable the fluid to leak therefrom.

B. Mesh Conformal with Balloon

Figure 57:
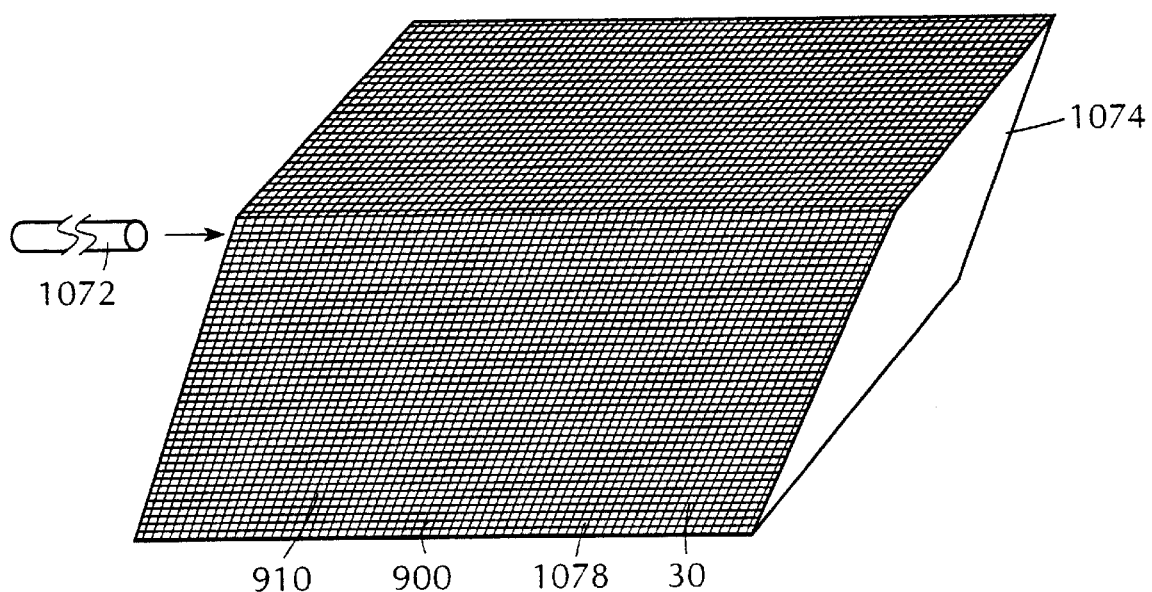
FIG. 57 depicts a tissue separating balloon of the present invention having one major surface formed from a plugged porous material which may be separated and emplaced within an operating space created thereby.
Figure 58:
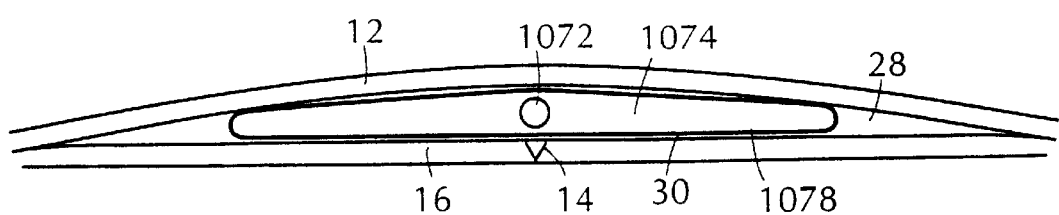
FIG. 58 depicts the tissue separating device of FIG. 57 being left in place within the operating space formed thereby.

The present invention also contemplates forming tissue-separating balloon 874 of the present invention to be separable from fluid conduit 72 and thereby emplaceable to remain over the myopectineal orifice 32 with the expanded prosthetic mesh 30. Referring still to FIGS. 57 and 58 and with additional reference to FIG. 58a, the present invention contemplates delivering a porous surgical prosthetic mesh 30 conformal with a tissue-separating balloon 874 of the present invention that is separable from fluid conduit 72 so that balloon 874 and prosthetic mesh 30 may be left in place over the myopectineal orifice 32. While reference is made to a mesh-delivery balloon 874, the present invention contemplates that each of the tissue-separating balloons of the present invention may be provided as emplaceable delivery balloons. For the sake of simplicity, only balloon 874 will be called out in the following description. Prosthetic mesh 30 is desirably laminated to balloon 874, although prosthetic mesh 30 may be adhered to balloon 874 by any means known in the art. Additionally, prosthetic mesh 30 is desirably laminated to balloon 874 at a number of distinct locations 904 along the perimetrical edge 902 thereof so as to maximize the number of pores 900 available for immediate tissue ingrowth once emplaced. While prosthetic mesh 30 is desirably adhered to balloon 874 only along its perimetrical edge 902 when balloon 874 is formed in accordance with tissue-separating balloon 374, other balloons of the present invention would also permit lamination at locations across a major surface thereof.

Figure 55A:
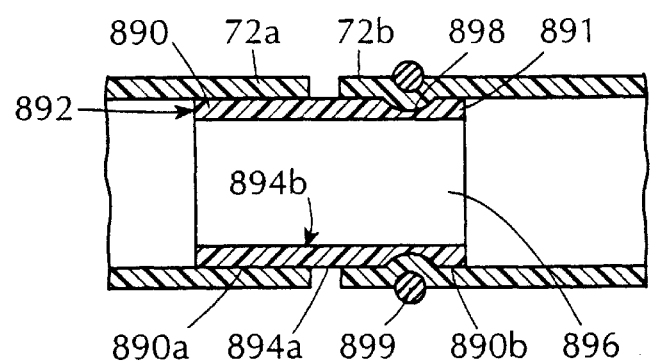
FIG. 55a depicts a separable connector design for the fluid conduit of the balloon of FIG. 55.

Emplacement of balloon 874 is desirably provided by modifying fluid conduit 72. As shown in FIG. 55a, fluid conduit 72 is severed adjacent to balloon 874 so as to provide a distal conduit end 72a and a balloon conduit end 72b. Balloon conduit end 72b is contiguous with balloon 874 and includes an inner passageway communicating with the balloon interior. An elongate hollow connector sleeve 890 is provided for joining conduit ends 72a and 72b in fluid communication. Sleeve 890 includes a hollow cylindrical wall 891 having a proximal end 890a, a distal end 890b and an elongate cylindrical wall 892 extending therebetween. Cylindrical wall 892 includes an outer surface 894a and a cylindrical inner surface 894b defining an elongate fluid passageway 896 through sleeve 890. Outer surface 894a includes an annular depression 898. Sleeve 890 is internally received within both conduit ends 72a and 72b. Conduit end 72 is adhered or otherwise affixed to outer surface 892a while conduit end 72b is removably fitted thereabout. A removable retaining means such as o-ring 899 is positioned over conduit end 72b in registry with annular depression 898 so as to provide a fluid tight and releasable connection between conduit end 72b and sleeve 890.

As tissue-separating balloon 874 is to be emplaced with and remain with the prosthetic mesh 30, balloon 874 is desirably formed from a biodegradable material that will decompose and be absorbed by the body as tissue grows through the pores of the emplaced prosthetic mesh 30. The terms "biodegradable" and "bioabsorbable" as used herein are given common meaning for the present invention and relate to the ability to be degraded by processes involving biological conditions, such as those present in the bodies of humans or other animals. More specifically, this term indicates the physical or chemical breaking down of the polymer into smaller units which are preferably innocuous, non-toxic, and are readily eliminated by the body. Balloon 874 therefore allows a mesh to be delivered simultaneously with the creation of operating space 28. It is contemplated that additional access ports may be provided so that additional small diameter cannulas may be inserted into operating space 28 for suturing prosthetic mesh 30 to the abdominal wall 12.

Alternatively, the present invention further contemplates that prosthetic mesh 30 may be delivered by an emplaceable tissue separating balloon 1074 wherein the prosthetic mesh 30 forms one major surface of that balloon. As shown in FIGS. 57–58, balloon 1074 may be formed in accordance with any of the balloons of the present invention providing a suitable major surface. Tissue separating balloon 1074 includes a first major surface 1078 formed by a porous surgical prosthetic mesh 30 having a plurality of pores 900 sealed fluid tight by a biodegradable filler 910. Balloon 1074 may perform the function of tissue-dissection simultaneously with the positioning of prosthetic mesh 30 over the herniated region 14. Balloon 1074 may be separated from fluid conduit 1072 for emplacement within operating space 28. A surgeon may suture, adhere, or otherwise affix balloon 1074 or just major surface 1078 to the abdominal wall 12 after the dissection and ligation of the hernia sac. Thereafter, the biodegradable material 910 filling the pores 900 of prosthetic mesh 30 will be absorbed by the body so as to expose the pores 900 and thereby provide for tissue ingrowth therethrough. The remainder of balloon 1074, being similarly made of a biodegradable material, will similarly dissolve for absorption by the body. As it is desirable to first expose pores 900 of prosthetic mesh 30 prior to assimilating mesh 30 within the body, biodegradable material 910 filling the pores 900 of prosthetic mesh 30 will be selected so as to break down prior to the biodegradable material forming prosthetic mesh 30 breaking down.

C. Mesh separately provided by guidewire

Referring now to FIGS. 59–65, the present invention also contemplates delivering a surgical mesh to an operating space 28 previously formed by a tissue dissection device.

Figure 64:
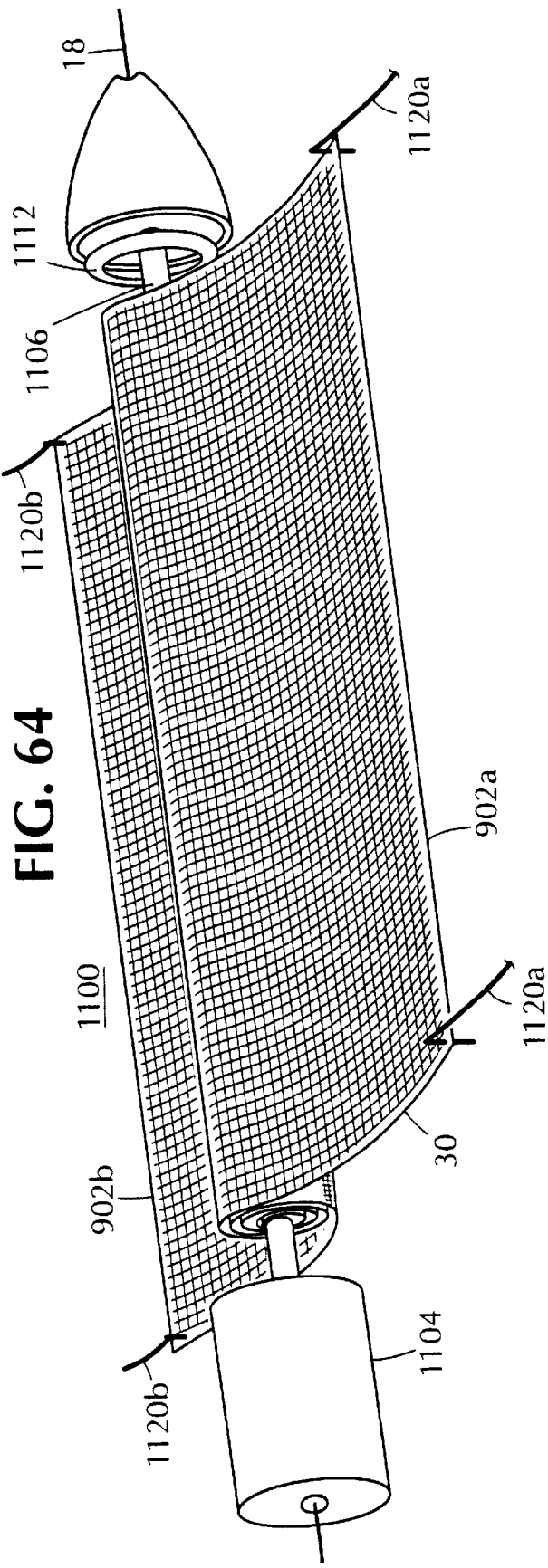

FIGS. 59, 62 and 64 depict a mesh delivery device 1100 for delivering prosthetic mesh 30 into operating space 28. Mesh delivery device 1100 is an elongate device having a blunt nose 1102 and a tubular body portion 1104 at opposite ends of a centrally located guidewire conduit 1106. Blunt nose 1102, body portion 1104 and guidewire conduit 1106 define a longitudinally extending guidewire passageway 1108 through device 1100 for accommodating guidewire 18. Device 1100 is formed of a rigid material such as metal or a suitable surgical plastic. Guidewire conduit 1106 is desirably centrally located so as to serve the dual purposes of accommodating guidewire 18 through device 1100 and to serve as a deployment axle for deployably wrapping a prosthetic mesh 30 thereabout. As shown in FIG. 59, device 1100 includes a retractable sheath 1110, shown by phantom lines, and a circumferential retaining means such as an elastic band 1112 positioned about prosthetic mesh 30 so as to maintain the furled configuration of prosthetic mesh 30 about guidewire conduit 1106 prior to mesh deployment.

Prosthetic mesh 30 is desirably a porous mesh material providing pores 900 for promoting tissue ingrowth therethrough and may be formed of a biodegradable material to be absorbed through the body after forming a new tissue layer over the herniated region. One particularly useful prosthetic mesh is disclosed by U.S. patent application Ser. No. 08/905,529 presently assigned to Meadox Medicals, Inc., a subsidiary of the present assignee and is incorporated by reference herein. FIGS. 60 and 61 depict two possible configurations for deployably wrapping prosthetic mesh 30 about guidewire conduit 1106. FIG. 60 depicts a configuration whereby one edge 902a of prosthetic mesh 30 is placed on guidewire 1106 and then prosthetic mesh 30 is then simply spooled thereabout. FIG. 61 depicts an alternate delivery configuration for prosthetic mesh 30 whereby prosthetic mesh 30 is longitudinally folded to provide a crease 912. While maintaining prosthetic mesh 30 in the folded configuration, crease 912 is positioned adjacent guidewire conduit 1106 and prosthetic mesh 30 is then spooled thereabout so as to desirably provide opposed edges 902a and 902b to diametrically opposite sides of guidewire conduit 1106.

Figure 65:
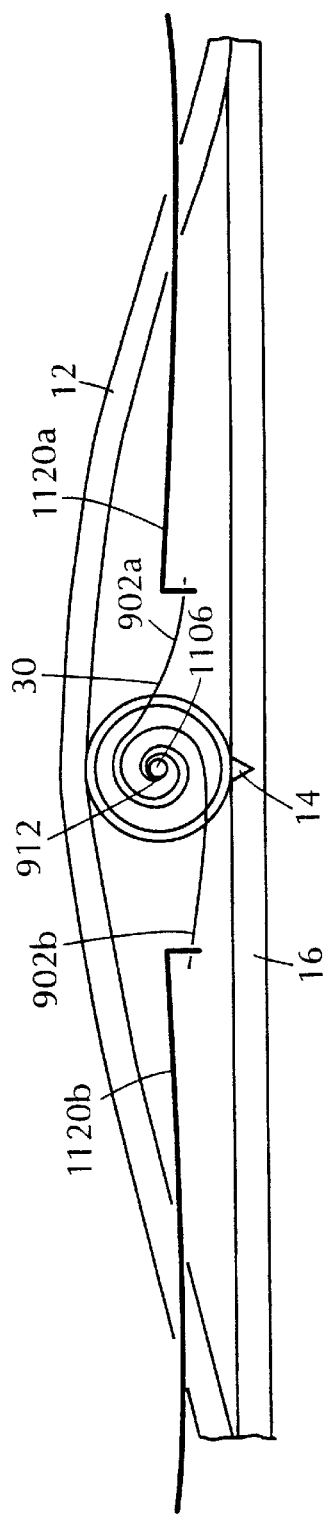

With reference to FIGS. 63 and 65, device 1100 may be delivered along guidewire 18 to a location within operating space 28. The operator then retracts sheath 1110 in the direction of arrow a so as to expose prosthetic mesh 30 to operating space 28. The operator then desirably provides an insufflation gas, such as carbon dioxide, so as to inflate operating space 28 for prosthesis deployment. Insufflation may be accomplished by any means well-known in the art. As shown in FIGS. 62 and 63, wherein guidewire 18 is desirably provided along one edge of operating space 28, the operator provides an entry port on the opposite side of operating space 28 for introducing an elongate unfurling probe 1120. Probe 1120 desirably includes transversely extending finger 1122 for grabbing and manipulating prosthetic mesh 30. Probe 1120 may also be used for pushing retainer 1112 clear of prosthetic mesh 30. The operator grabs the free edge 90b of prosthetic mesh 30 with probe finger 1122. The operator desirably provides a second elongate unfurling probe 1124 having a transversely-extending finger 1126 so that opposing ends of the exposed edge 90b of prosthetic mesh 30 may be simultaneously pulled so as to unfurl prosthetic mesh 30 from device 1100 while simultaneously positioning prosthetic mesh 30 within operating space 28. Prosthetic mesh 30 may then be sutured or stapled in place over the herniated region 14.

FIGS. 64 and 65 depict the unfurling of prosthetic mesh 30 when it is furled about guidewire conduit 1106 as shown in FIG. 60. With prosthetic mesh 30 so furled, device 1100 is desirably provided along a guidewire 18 centrally positioned within operating space 28. The operator insufflates operating space 28 using conventional techniques and provides access ports 1140 and 1142 transversely spaced from device 1100 for introducing deployment prongs 1120a and 1120b. With this configuration the operator may grab the opposing edges 902a and 902b of prosthetic mesh 30 and pull each in opposite directions to thereby unfurl the prosthesis within operating space 28. The operator may use prongs 1120a and 1120b to fully deploy the prosthesis prior to suturing or stapling the prosthesis in place over the herniated region 14.

Referring to FIG. 66, it is also contemplated by the present invention to provide a prosthetic mesh 30 rolled within the interior passageway 1202 of an elongate delivery needle 1200. Delivery needle 1200 includes an elongate ejection plunger 1204 slidable within passageway 1202 towards an ejection end 1200a of needle 1200. Ejection end 1200a may be provided within operating space 28 so that prosthetic mesh 30 may be ejected thereinto by pushing plunger 1204 and unfurled by the operator. It is further contemplated that prosthetic mesh 30 may include a self-opening element for automatically deploying within operating space 28 over the herniated region 14.

Regardless of the method used for deploying a prosthesis of the present invention it is felt that reinforcement in this area with a surgical mesh allows intra-abdominal pressure to assist in securing the inlayed prosthesis to the pelvic floor rather than acting as a factor in recurrence. After mesh placement, the peritoneum becomes nondistensible, and thus there is no need for hernia defect closure.

While the present invention has been shown and described in detail above, it will be clear to the person skilled in the art that changes and modifications may be made without departing from the spirit and scope of the invention. That which is set forth in the foregoing description and accompanying drawings is offered by way of illustration only and not as a limitation. The actual scope of the invention is intended to be defined by the following claims.

What is claimed is:

1. An instrument for creating an operating space in a body comprising:
    an elongate cannula body having a blunt nose, an elongate side wall defining an access aperture, an interior lumen, and a first elongate deployment aperture, said cannula being deliverable along a guidewire between a first and second tissue layer in a body;
    a retractable outer protective sheath,
    a fluid delivery lumen in fluid communication with a fluid source, and
    a hollow expandable tissue separating balloon including a first deployable tissue separating wing having a first major surface and a second major surface, said first major surface being peripherally contiguous with said second major surface across a distal end, said first and second major surfaces defining a fluid-tight balloon cavity therebetween, said balloon cavity being in fluid communication with said fluid delivery lumen and expandable through said first deployment aperture of said cannula body from a first contracted configuration confined within said cannula body to a second expanded configuration extending through said elongate window so as to form said operating space between said first and second tissue layers, wherein one of said first and second major surfaces of said tissue separating balloon comprises a porous prosthetic mesh so that, upon tissue separating balloon expansion, said mesh will be deployed over said operating area.

2. The instrument of claim 1, wherein said balloon is disconnectably connected to said fluid delivery lumen for placement in said operating space.

3. The instrument of claim 1, wherein said mesh is separable from said one of said first and second major surfaces of said tissue separating balloon over said operating area.

4. The instrument of claim 1, wherein said mesh is laminated to said tissue separating balloon.

5. The instrument of claim 1, wherein said porous mesh is sealed with a biodegradable material to maintain the fluid integrity of said tissue separating balloon during expansion thereof to the extended configuration, said tissue separating balloon being emplaceable over the operating area so as to position said mesh over said operating area as the biodegradable material decomposes.

6. The instrument of claim 1, wherein said device is insertable through a trocar having a diameter of 10 millimeters or less.

7. The instrument of claim 1, wherein said device is insertable through a trocar having a diameter of 5 millimeters or less.

8. A balloon for delivering a surgical mesh to an operating space between adjacent layers of tissue comprising:
    a balloon body including;
    a fluid entry port disconnectably connected to a fluid delivery source;
    a first major surface;
    a second major surface in facing opposition to, and peripherally contiguous with, said first major surface to define a fluid tight interior space in fluid communication with said fluid entry port;
    a porous surgical mesh coextensive with one of said first and second major surfaces whereby said surgical mesh may be deployed over an operating site by delivering a fluid through said fluid entry port into said interior space to expand said balloon from a contracted configuration to an expanded configuration and disconnecting said balloon at said fluid entry port from said fluid delivery source.

9. The balloon of claim 8, wherein one of said first and second major surfaces further comprises said porous mesh having a biodegradable filling material extending into the pores of said mesh to maintain the fluid integrity of said fluid tight interior space, whereby decomposition of said biodegradable filling exposes the pores of said mesh to permit tissue ingrowth therethrough.

10. The balloon of claim 9, wherein said other of said first and second major surfaces is formed of a biodegradable material so as to decompose once positioned over said operating site.

11. The balloon of claim 10, wherein said first and second major surfaces form an elongate tubular outer balloon wall having a first segment, a second segment, a third segment, and a fourth segment in serial fluid communication.

12. The balloon of claim 11, wherein said first and third segments extend substantially transverse to said second and fourth segments.

13. The balloon of claim 12 wherein said first and third segments extend transversely with respect to an elongate cannula body having a blunt nose, an elongate side wall defining an access aperture, an interior lumen, and a first elongate deployment aperture, said cannula being deliverable along a guidewire between a first and second tissue layer in a body.

14. A device for delivering a surgical prosthetic mesh to an operating space comprising:
- an elongate cannula body having an elongate cylindrical cannula wall having a first outside diameter and being able to accommodate a guidewire therethrough,
- an elongate cylindrical guidewire conduit supported by said cannula wall having a second smaller outside diameter and an interior passageway therethrough for accommodating the guidewire,
- a blunt nose supported by said guidewire conduit including a cylindrical rim having the first outside diameter as the cylindrical cannula wall and an interior nose passageway communicating with said interior passageway of said guidewire conduit, wherein said cylindrical rim is offset from said cannula wall to define an elongate cannula window and a cylindrical mesh delivery area about the guidewire conduit between said cannula wall and said blunt nose, and
- an elongate retractable sheath extending along the outside of the cylindrical cannula wall to the surface of the rim of the blunt nose,
- wherein a prosthetic mesh having a pair of opposed elongate edges is deployably wrapped about said guidewire conduit such that retraction of said sheath exposes said prosthetic mesh.

15. The device of claim 14 wherein the mesh is deployably wrapped about said guidewire conduit by placing one edge of the mesh along the guidewire conduit and then furling the mesh about thereabout so as expose the opposed edge of the mesh, wherein the exposed edge of the mesh may be grasped and transversely pulled to deploy the mesh within the operating space.

16. The device of claim 14, wherein the mesh is longitudinally folded about a crease so that the opposed edges of the mesh are brought towards each other, said crease being placed along the guidewire conduit and the mesh being furled about the guidewire conduit so as to provide the opposed edges to either side of the guidewire conduit, whereby simultaneously grasping and pulling the opposed edges in opposite directions deploys the mesh within the operating space.

17. The device of claim 14, wherein said mesh further includes comprises a length of suturing material having a first end connected to an edge of said mesh and second end being graspable from said operating area.

18. The device of claim 14, wherein said first diameter is about 10 millimeters or less.

19. The device of claim 14, wherein said first diameter is about 5 millimeters or less.

20. The device of claim 14, wherein said first diameter is about 2 millimeters or less.

* * * * *

UNITED STATES PATENT AND TRADEMARK OFFICE
CERTIFICATE OF CORRECTION

PATENT NO. : 6,258,113 B1
DATED : July 10, 2001
INVENTOR(S) : Adams, R.

It is certified that error appears in the above-identified patent and that said Letters Patent is hereby corrected as shown below:

<u>Title page,</u>
Under Inventors, "Ronald D. Adams, Holliston; William J. Shaw, Cambridge, both of MA (US)", should read -- Ronald D. Adams, Holliston, MA (US) --.

Signed and Sealed this

Twenty-ninth Day of January, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.   : 6,258,113 B1
DATED        : July 10, 2001
INVENTOR(S)  : Adams, R.

It is certified that error appears in the above-identified patent and that said Letters Patent is hereby corrected as shown below:

Title page,
Attorney, Agent or Firm, the printed patent incorrectly reads, "Hoffman & Baron, LLP". The printed patent should read -- Hoffmann & Baron, LLP --, as evidenced by the Issue Fee Transmittal.

Column 20,
Line 16, the printed patent incorrectly reads "only balloon 814". The patent should read -- only balloon 874 --.
Line 25, the printed patent incorrectly reads "or stapling ox". The patent should read -- or stapling or --.
Line 29, the printed patent incorrectly reads "draining of die inflating". The patent should read -- draining of the inflating --.

Signed and Sealed this

Twenty-sixth Day of March, 2002

JAMES E. ROGAN
Director of the United States Patent and Trademark Office

Attest:

Attesting Officer